United States Patent
Suzuki et al.

(10) Patent No.: US 8,648,905 B2
(45) Date of Patent: Feb. 11, 2014

(54) TRANSPARENT BODY INSPECTING DEVICE

(75) Inventors: Toshihiko Suzuki, Tokyo (JP);
Hidetoshi Matsumoto, Tokyo (JP);
Munehisa Kato, Tokyo (JP); Makoto Kurumisawa, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 153 days.

(21) Appl. No.: 13/112,576

(22) Filed: May 20, 2011

(65) Prior Publication Data
US 2011/0221885 A1    Sep. 15, 2011

Related U.S. Application Data

(63) Continuation of application No. PCT/JP2009/069459, filed on Nov. 16, 2009.

(30) Foreign Application Priority Data

Nov. 20, 2008  (JP) ................................. 2008-297112
Nov. 20, 2008  (JP) ................................. 2008-297113

(51) Int. Cl.
*H04N 7/18* (2006.01)
(52) U.S. Cl.
USPC .......................................................... 348/125
(58) Field of Classification Search
USPC .............................. 348/125; 356/237.1, 239.1
See application file for complete search history.

(56) References Cited

U.S. PATENT DOCUMENTS 5,790,247 A *  8/1998  Henley et al. .............. 356/237.1
2005/0259248 A1  11/2005  Gip et al.
2006/0098190 A1*  5/2006  Miyake et al. ............. 356/239.1

FOREIGN PATENT DOCUMENTS

| JP | 6-294749 | 10/1994 |
|---|---|---|
| JP | 2000-193598 | 7/2000 |
| JP | 2002-98650 | 4/2002 |
| JP | 2004-309426 | 11/2004 |
| JP | 2005-331515 | 12/2005 |
| JP | 2006-133042 | 5/2006 |
| JP | 2007-163315 | 6/2007 |

OTHER PUBLICATIONS

Japanese International Search Report mailed Feb. 16, 2010 in PCT/JP2009/069459 filed Nov. 16, 2009 (with English Translation).

* cited by examiner

*Primary Examiner* — Sath V Perungavoor
*Assistant Examiner* — James Pontius
(74) *Attorney, Agent, or Firm* — Oblon, Spivak, McClelland, Maier & Neustadt, L.L.P.

(57) ABSTRACT

A transparent body inspecting device includes a light application unit, an image capturing unit, an image capture driving unit, and a defect determining unit. The image capturing unit is moved in the directions in which the image capturing unit is brought close to and away from the upper surface of the transparent body, and the image capturing unit captures a plurality of images of the transparent body during the movement. The images are captured while the position of the depth of field of the image capturing unit is adjusted to more than one spots inside the transparent body. When brightness of pixels in the captured image is nonuniform, the defect determining unit determines that a defect exists within the depth of field at the time of capture of the image.

5 Claims, 17 Drawing Sheets

DEPTH OF FIELD

FIG. 3
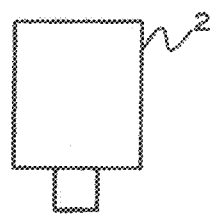
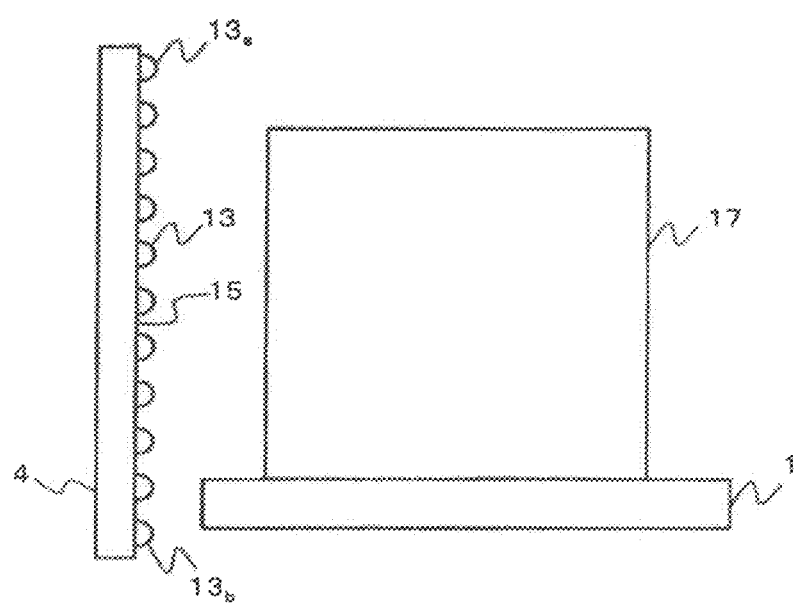

FIG. 11
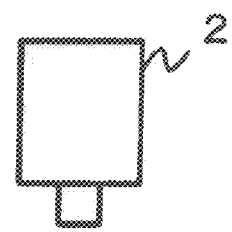
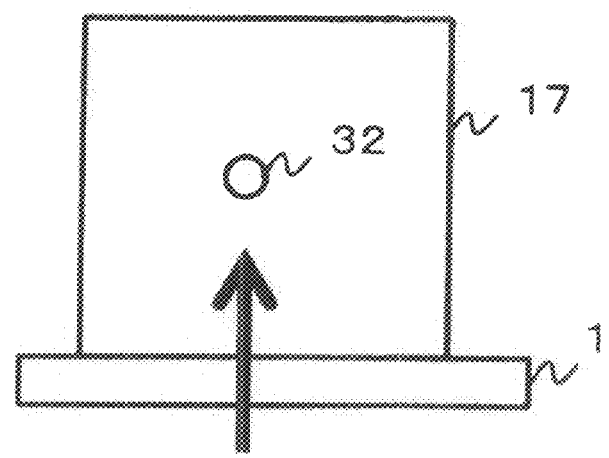

TRANSPARENT BODY INSPECTING DEVICE

TECHNICAL FIELD

The present invention relates to a transparent body inspecting device, and in particular relates to a transparent body inspecting device for inspecting a transparent body having no birefringence.

BACKGROUND ART

Inspection methods for inspecting transparent bodies include a plate glass defect inspection method disclosed in Patent Document 1. In the plate glass defect inspection method disclosed in Patent Document 1, plate glass is illuminated from its lateral end face, and an image of a plate glass surface is captured by an image capturing optical system from the surface side of the plate glass to detect brightness of the image per given area, thus determining a defect. This inspection method utilizes a phenomenon in which when an internal defect such as a bubble or a foreign substance exists in the plate glass, light is irregularly reflected by the defect and emitted outside from upper and lower surfaces of the plate glass.

Patent Document 1 further discloses a method in which an illumination light source is placed adjacent to one side of plate glass, an image capturing optical system is placed adjacent to the other side of the plate glass, an image of the plate glass is captured by the image capturing optical system, and the image formed based on transmitted light is processed, thus detecting a defect.

Moreover, Patent Document 2 discloses a transparent body detection system for detecting a transparent foreign substance inside a transparent bottle (which is an empty bottle or a bottle containing transparent liquid). The transparent body detection system disclosed in Patent Document 2 includes: an illumination device for applying planar light to the bottle that is vertically put; and a light projection side polarizing plate, provided over a light projection surface of the illumination device, for polarizing the planar light in a particular direction. The system further includes a light receiving polarizing plate and a television camera, which are located opposite to the light projection side polarizing plate with the bottle located at the center. The light projection side polarizing plate and the light receiving polarizing plate are set so that polarization directions thereof coincide with each other. The transparent body detection system disclosed in Patent Document 2 rotates the bottle, captures images thereof repeatedly by the television camera during one rotation of the bottle, and determines existence of a transparent foreign substance when the image captured by the television camera has a region where a dark chunk is seen. Furthermore, Patent Document 2 also discloses a case in which the light projection side polarizing plate and the light receiving polarizing plate are set so as to be orthogonal to each other, and existence of a transparent foreign substance is determined when an image has a region where a bright chunk is seen. Besides, Patent Document 2 discloses a slide actuator for sliding the polarizing plate within a horizontal plane, and a slide actuator controller for driving and controlling the slide actuator.

PRIOR ART REFERENCE

Patent Document

Patent Document 1: JP-A-H6-294749 (Paragraphs [0024] and [0035], and FIGS. 1, 3 and 9)

Patent Document 2: JP-A-2002-98650 (Paragraphs [0081] to [0098], FIGS. 22 to 24, Paragraph [0062], and FIG. 14)

DISCLOSURE OF THE INVENTION

Problems to be Solved by the Invention

In the invention disclosed in Patent Document 1, existence or nonexistence of a defect can be inspected. However, even when existence of a defect could be determined, it was impossible to determine the depth of a position, at which the defect exists, from the surface of the plate glass.

When an inspection object has a large thickness, it is preferable to determine not only the position of a defect within a plane extending along a surface of the inspection object but also the depth of a position, at which the defect exists, from the surface. However, the method disclosed in Patent Document 1 falls short of determining the depth of a position at which a defect exists.

Further, in the invention disclosed in Patent Document 2, existence or nonexistence of a transparent foreign substance inside the transparent bottle can be inspected. However, also in the invention disclosed in Patent Document 2, it was impossible to determine the depth of a position, at which a defect (transparent foreign substance) exists, from the surface of the inspection object.

Furthermore, defects inside a transparent body can be classified into three types. A first defect is a defect that scatters light. Specifically, the first defect is a defect that scatters light incident on the inside of the transparent body and traveling through the transparent body. A second defect is a defect that blocks light. Specifically, the second defect is a defect that blocks light incident on the inside of the transparent body and traveling through the transparent body. A third defect is a defect that changes a refractive index inside the transparent body. Hereinafter, the first defect will be referred to as a "scattering defect", and the second defect will be referred to as a "light-blocking defect". Moreover, the third defect may also be described as a defect that causes polarization cancellation, and will hereinafter be referred to as a "polarization cancellation defect".

Patent Document 1 discloses the inspection method in which the plate glass is illuminated from its lateral end face, and an image of the plate glass surface is captured by the image capturing optical system from the surface side of the plate glass. With the use of an apparatus for performing inspection by this method, existence or nonexistence of a scattering defect can be determined.

Patent Document 1 further discloses the inspection method in which the illumination light source is placed adjacent to one side of the plate glass, the image capturing optical system is placed adjacent to the other side of the plate glass, and an image of the plate glass is captured by the image capturing optical system. With the use of an apparatus for performing inspection by this method, existence or nonexistence of a light-blocking defect can be determined.

Furthermore, with the use of the apparatus disclosed in Patent Document 2, existence or nonexistence of a birefringence defect can be determined.

However, when a plurality of apparatuses are used and existence or nonexistence of one type of a defect is determined by each apparatus, an inspection object has to be transferred to the other apparatuses in order to inspect existence or nonexistence of a plurality of types of defects. Hence, it takes time to finish the inspection.

Therefore, an object of the present invention is to provide a transparent body inspecting device capable of determining, when a defect exists inside a transparent body serving as an inspection object, the depth of a position at which the defect exists.

Another object of the present invention is to provide a transparent body inspecting device capable of determining existence or nonexistence of a plurality of types of defects.

Solution to the Problems

A first aspect of the present invention provides a transparent body inspecting device including: a light application unit (e.g., a first light source 4 or a second light source 5) for applying light to a transparent body; an image capturing unit (e.g., an image capturing unit 2) which captures an image of the transparent body and in which a depth of field is smaller than a height of the transparent body; a image capture driving unit (e.g., an image capture driving unit 3) for moving the image capturing unit in a direction in which the image capturing unit is brought close to the transparent body and in a direction in which the image capturing unit is brought away from the transparent body; and a defect determining unit (e.g., a defect determining unit 12) for determining existence or nonexistence of a defect in the transparent body based on whether or not brightness of pixels in the image captured by the image capturing unit is nonuniform, wherein the image capturing unit carries out image capture more than once while moving in the direction in which the image capturing unit is brought close to the transparent body or in the direction in which the image capturing unit is brought away from the transparent body, and wherein when the brightness of pixels in the image captured by the image capturing unit is nonuniform, the defect determining unit determines that a defect exists within the depth of field at the time of capture of this image.

A second aspect of the present invention provides a transparent body inspecting device based on the first aspect, wherein when defective capture images having nonuniform brightness of pixels are continuous in a plurality of the images captured by the image capturing unit while the image capturing unit is moved in one direction, the defect determining unit determines that a defect exists within the depth of field at the time of capture of the defective capture image having the highest contrast among the defective capture images.

A third aspect of the present invention provides a transparent body inspecting device based on the first or second aspect, wherein when the image capturing unit is moved in the direction in which the image capturing unit is brought close to the transparent body and in the direction in which the image capturing unit is brought away from the transparent body, the image capture driving unit moves the image capturing unit with constant velocity, and wherein the image capturing unit captures images of the transparent body while moving with constant velocity.

A fourth aspect of the present invention provides a transparent body inspecting device based on any one of the first to third aspects, wherein the transparent body inspecting device includes, as the light application unit, at least a light application unit (e.g., the first light source 4) having a lateral wall which is perpendicular to an upper surface of the transparent body and on which a plurality of point light sources are arranged, and wherein the point light source (e.g., a point light source $13_a$) at an end portion close to the image capturing unit is located closer to the image capturing unit than a surface of the transparent body, which faces toward the image capturing unit, and the point light source (e.g., a point light source $13_b$) at an end portion away from the image capturing unit is located further away from the image capturing unit than a surface of the transparent body, which is opposite to the image capturing unit.

A fifth aspect of the present invention provides a transparent body inspecting device based on the fourth aspect, wherein the plurality of point light sources are aligned in a plurality of rows and arranged so that positions of the point light sources in the adjacent rows are deviated from each other.

A sixth aspect of the present invention provides a transparent body inspecting device including: an image capturing unit (e.g., the image capturing unit 2) for capturing an image of a transparent body; a first light application unit (e.g., the first light source 4) for applying light to the transparent body from a lateral position; a second light application unit (e.g., the second light source 5) for applying light to the transparent body from a position located opposite to the image capturing unit, with the transparent body sandwiched between the image capturing unit and the second light application unit; and a defect determining unit (e.g., the defect determining unit 12) for determining existence or nonexistence of a defect in the transparent body based on whether or not brightness of pixels in the image captured by the image capturing unit is nonuniform, wherein the defect determining unit determines whether or not the brightness of pixels in the image, captured in a state in which light is applied to the transparent body by the first light application unit, is nonuniform, and also determines whether or not the brightness of pixels in the image, captured in a state in which light is applied to the transparent body by the second light application unit, is nonuniform, thus determining existence or nonexistence of a plurality of types of defects.

A seventh aspect of the present invention provides a transparent body inspecting device based on the sixth aspect, wherein the second light application unit applies polarized light, wherein the transparent body inspecting device includes: a polarizing plate (e.g., an image capture side polarizing plate 8) for blocking the polarized light applied from the second light application unit and traveling toward the image capturing unit; a polarizing plate driving unit (e.g., a polarizing plate driving unit 10) for changing a positional state of the polarizing plate; and a determination type switching unit (e.g., a switching unit 11) for allowing at least the first light application unit to apply light at the time of capture of a scattering determination image serving as an image by which existence or nonexistence of a scattering defect for scattering light is determined, for allowing the first light application unit to stop light application while allowing the second light application unit to apply polarized light and allowing the polarizing plate driving unit to position the polarizing plate so as to allow passage of the polarized light traveling toward the image capturing unit at the time of capture of a light blockage determination image serving as an image by which existence or nonexistence of a light-blocking defect for blocking light is determined, and for allowing the first light application unit to stop light application while allowing the second light application unit to apply polarized light and allowing the polarizing plate driving unit to position the polarizing plate so as to block the polarized light traveling toward the image capturing unit at the time of capture of a polarization cancellation determination image serving as an image by which existence or nonexistence of a polarization cancellation defect for changing a refractive index of part of the transparent body is determined, and wherein the defect determining unit determines that a scattering defect exists when brightness of pixels in the scattering determination image is nonuniform, determines that a light-blocking defect exists when brightness of pixels in the light blockage determination image is nonuniform, and determines that a polarization cancellation defect exists when brightness of pixels in the polarization cancellation determination image is nonuniform.

An eighth aspect of the present invention provides a transparent body inspecting device based on the sixth aspect, wherein the first light application unit applies light of a first wavelength, wherein the second light application unit applies polarized light of a second wavelength polarized in a particular direction (e.g., a P wave of the second wavelength) and polarized light of a third wavelength polarized in a particular direction (e.g., a P wave of the third wavelength), wherein the transparent body inspecting device includes a polarized light beam splitter (e.g., a polarized light beam splitter 28) that reflects the polarized light of the third wavelength polarized in the particular direction, and that allows passage of light of a wavelength other than the third wavelength, and polarized light of the third wavelength polarized in a direction other than the particular direction (e.g., light other than a P wave, such as an S wave of the third wavelength), wherein the image capturing unit captures images of the transparent body in a state in which the light of the first to third wavelengths is simultaneously applied from the first light application unit and the second light application unit, and wherein the defect determining unit determines that a defect for scattering light exists when brightness of pixels, included in the image captured by the image capturing unit and having a color corresponding to the first wavelength, is nonuniform, determines that a defect for blocking light exists when brightness of pixels included in the image and having a color corresponding to the second wavelength is nonuniform, and determines that a defect for changing a refractive index of part of the transparent body exists when brightness of pixels included in the image and having a color corresponding to the third wavelength is nonuniform.

A ninth aspect of the present invention provides a transparent body inspecting device based on the eighth aspect, wherein the first light application unit applies blue light as the light of the first wavelength, and wherein the second light application unit applies polarized green light as the polarized light of the second wavelength, and applies polarized red light as the polarized light of the third wavelength.

A tenth aspect of the present invention provides a transparent body inspecting device based on any one of the sixth to ninth aspects, wherein the transparent body inspecting device includes: a storage unit (e.g., a result storage unit 52) for storing a parameter (e.g., a production condition) for a production process of the transparent body and a determination result obtained by the defect determining unit; and a determination result registration unit (e.g., a determination result registration unit 51) to which the parameter is inputted and through which the parameter and the determination result obtained by the defect determining unit are stored in the storage unit.

An eleventh aspect of the present invention provides a transparent body inspection method including: applying light to a transparent body; capturing a plurality of images of the transparent body while an image capturing unit in which a depth of field is smaller than a height of the transparent body is moved in a direction in which the image capturing unit is brought close to the transparent body and in a direction in which the image capturing unit is brought away from the transparent body; and determining, when brightness of pixels in the image captured by the image capturing unit is nonuniform, that a defect exists within the depth of field at the time of capture of this image.

A twelfth aspect of the present invention provides a transparent body inspection method including: applying light to a transparent body from a lateral position; applying light to the transparent body from a position located opposite to image capturing unit for capturing an image of the transparent body, with the transparent body sandwiched between the image capturing unit and the position opposite thereto; and determining whether or not brightness of pixels in the image, captured by the image capturing unit in a state in which light is applied to the transparent body from the lateral position, is nonuniform, and determining whether or not brightness of pixels in the image, captured by the image capturing unit in a state in which light is applied to the transparent body from the opposite position, is nonuniform, thus determining existence or nonexistence of a plurality of types of defects.

Advantage of the Invention

According to the present invention, it is possible to determine, when a defect exists inside a transparent body serving as an inspection object, the depth of a position at which the defect exists.

Further, according to the present invention, it is possible to determine existence or nonexistence of a plurality of types of defects by a single apparatus, and thus it is possible to avoid an operation for transferring an inspection object to another inspection apparatus. Furthermore, the time required to inspect all of the plurality of types of defects can be consequently reduced.

BRIEF DESCRIPTION OF THE DRAWINGS

FIG. 3 is an explanatory diagram illustrating a positional relationship between a first light source and a transparent body.

FIG. 11 is an explanatory diagram illustrating a traveling state of light upon existence of a light-blocking defect when light blockage determination image capture setting is made.

MODE FOR CARRYING OUT THE INVENTION

Hereinafter, embodiments of the present invention will be described with reference to the drawings.

Each of the following embodiments will be described using, by way of example, a transparent body inspecting device for determining existence or nonexistence of each of a scattering defect, a light-blocking defect and a polarization cancellation defect.

The transparent body inspecting device according to the present invention uses, as an inspection object, a transparent body having no birefringence. Further, a transparent body formed into a film or flat plate shape by drawing has birefringence and is therefore not included in inspection objects for the transparent body inspecting device according to the present invention. Note that a transparent body having a birefringence index of 0.3 nm/cm or less may be defined as a transparent body having no birefringence. Specific examples of a transparent body having no birefringence include synthetic silica glass. Hereinafter, each embodiment of the present invention will be described.

Figure 1:
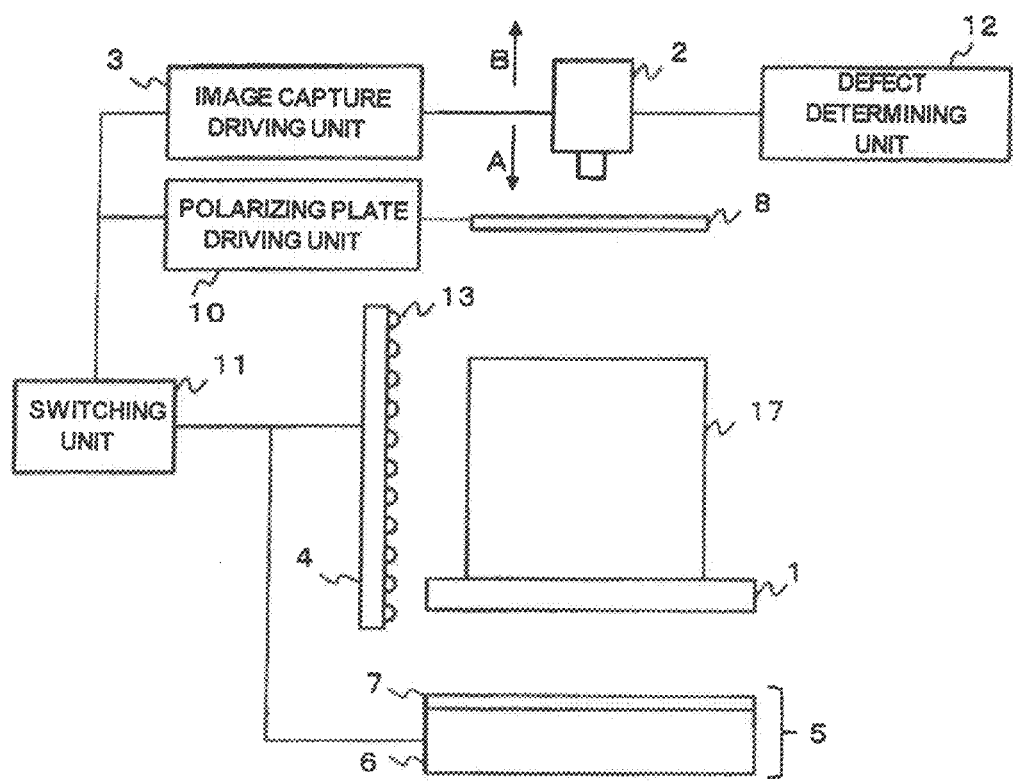
FIG. 1 is a block diagram illustrating an example of a first embodiment according to the present invention.

FIG. 1 is a block diagram illustrating an example of a first embodiment according to the present invention. A transparent body inspecting device according to the first embodiment includes: a support unit 1; an image capturing unit 2; an image capture driving unit 3; a first light source 4; a second light source 5; a polarizing plate 8; a polarizing plate driving unit 10; a switching unit 11; and a defect determining unit 12.

A transparent body 17 illustrated in FIG. 1 is a transparent body such as synthetic silica glass serving as an inspection object. Any transparent body other than synthetic silica glass may be placed as an inspection object as long as the transparent body has no birefringence. The transparent body 17 is a columnar block such as a circular cylinder and is placed on the support unit 1 so that one surface of the transparent body 17, i.e., an upper surface or a bottom surface thereof, faces toward the image capturing unit 2 and the other surface of the transparent body 17 faces toward the second light source 5. The transparent body 17 has a height of several tens of mm to several hundreds of mm, for example. However, this height is illustrative and the height of the transparent body 17 is not limited to this height.

The support unit 1 is a transparent support member for supporting the transparent body 17 from below. Since the support unit 1 is transparent, light applied from a lower end portion of the first light source 4 and light applied from the second light source are allowed to transmit through the support unit toward the transparent body 17.

Figure 2:
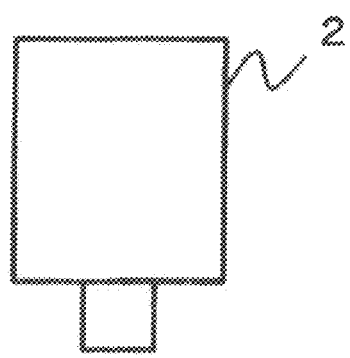
FIG. 2 is an explanatory diagram illustrating a depth of field.

The image capturing unit 2 captures an image of the transparent body 17 serving as an inspection object. The image capturing unit 2 is implemented by a camera including an image capturing element. A depth of field of the image capturing unit 2 is smaller than the height of the transparent body 17 (i.e., the height of the columnar block). The depth of field is a range in which the image capturing unit 2 focuses. FIG. 2 is an explanatory diagram illustrating the depth of field. The image capturing unit 2 carries out image capture while focusing on an object that exists within the range of the depth of field. Accordingly, an image of an object that exists within the depth of field becomes a focused image, but an image of an object that exists outside the depth of field becomes an unfocused image.

The image capture driving unit 3 is a driving device for moving the image capturing unit 2, and moves the image capturing unit 2 in a direction in which the image capturing unit 2 is brought close to the upper surface of the transparent body 17 and in a direction in which the image capturing unit 2 is brought away from the upper surface of the transparent body 17. In other words, the image capturing unit 2 is moved in directions A and B indicated by the arrows in FIG. 1. The image capturing unit 2 captures an image of the transparent body while being driven and moved by the image capture driving unit 3. Specifically, when the image capturing unit 2 is moved in the direction in which the image capturing unit 2 is brought close to the upper surface of the transparent body and in the direction in which the image capturing unit 2 is brought away from the upper surface of the transparent body, the image capture driving unit 3 moves the image capturing unit 2 with constant velocity, and the image capturing unit 2 repeatedly captures images of the transparent body 17 at given time intervals while being moved with constant velocity. With the movement of the image capturing unit 2, the position of the depth of field (see FIG. 2) is also moved. Accordingly, the image capturing unit 2 is capable of capturing images of inside of the transparent body 17 at various depths.

Furthermore, the image capture driving unit 3 also moves the image capturing unit 2 in a direction parallel to the upper surface of the transparent body 17. The image capture driving unit 3 moves the image capturing unit 2 to various positions within a plane of the transparent body 17, and moves, from these positions, the image capturing unit 2 in the directions A an B indicated by the arrows in FIG. 1.

As illustrated in FIG. 1, the first light source 4 is located laterally of the transparent body 17, and applies light to the transparent body 17 from a lateral position. In this embodiment, the description is made based on an example in which the image capturing unit 2 is located at a vertical position with respect to the upper surface of the transparent body 17 as illustrated in FIG. 1. Accordingly, in the present example, the first light source 4 applies light to the transparent body in a direction deviated by 90 degrees with respect to an optical axis direction of the image capturing unit 2.

As illustrated in FIG. 1, the first light source 4 has a lateral wall extended perpendicularly with respect to the upper surface of the transparent body 17. The lateral wall of the first light source 4 is also extended perpendicularly with respect to a surface (support surface) of the support unit 1 at which the transparent body 17 is supported. The first light source 4 is provided, at its lateral wall, with a plurality of point light sources 13, and applies light to the transparent body 17 from each point light source 13. Each point light source 13 applies, from the point light source itself, light in each direction in which the light is not blocked by a lateral wall 15. In other words, the first light source 4 does not apply light having directivity but applies light in various directions such as a horizontal direction and an oblique direction.

FIG. 3 is an explanatory diagram illustrating a positional relationship between the first light source 4 and the transparent body 17 supported by the support unit 1. Note that in FIG.

3, diagrammatic representation of the polarizing plate 8 illustrated in FIG. 1 is omitted. In the example described in the present embodiment, the height of the lateral wall 15 on which the point light sources 13 are arranged is greater than that of the transparent body 17. Accordingly, of the point light sources 13 arranged on the lateral wall 15, a point light source $13_a$ at an end portion close to the image capturing unit 2 is located closer to the image capturing unit 2 than the surface of the transparent body 17, which faces toward the image capturing unit 2. In other words, the point light source $13_a$ located at an upper end exists at a position higher than that of the surface of the transparent body 17, which faces toward the image capturing unit 2. Further, light applied from the point light source $13_a$ in an obliquely downward direction is allowed to be incident on the transparent body 17. Similarly, of the point light sources 13 arranged on the lateral wall 15, a point light source $13_b$ at an end portion away from the image capturing unit 2 is located further away from the image capturing unit 2 than the surface of the transparent body 17, which is opposite to the image capturing unit 2. In other words, the point light source $13_b$ located at a lower end exists at a position lower than that of the surface of the transparent body 17, which is opposite to the image capturing unit 2. Furthermore, light applied from the point light source $13_b$ in an obliquely upward direction is allowed to be incident on the transparent body 17. In this case, since the support unit 1 for supporting the transparent body 17 from below is transparent, light applied from the lower point light source is allowed to be passed through the support unit 1 and incident on the transparent body 17.

Thus, light is applied from a plurality of the point light sources 13 arranged in a range greater than the height of the transparent body 17, and therefore, the diversity of directions of light incident on the transparent body 17 and traveling through the transparent body 17 can be ensured. The lateral wall 15 and the transparent body 17 do not necessarily have to have a relationship in which the height of the lateral wall 15 on which the point light sources 13 are arranged is greater than that of the transparent body 17; however, in order to ensure the above-mentioned light direction diversity, the height of the lateral wall 15 on which the point light sources 13 are arranged is preferably greater than that of the transparent body 17.

Figure 4:
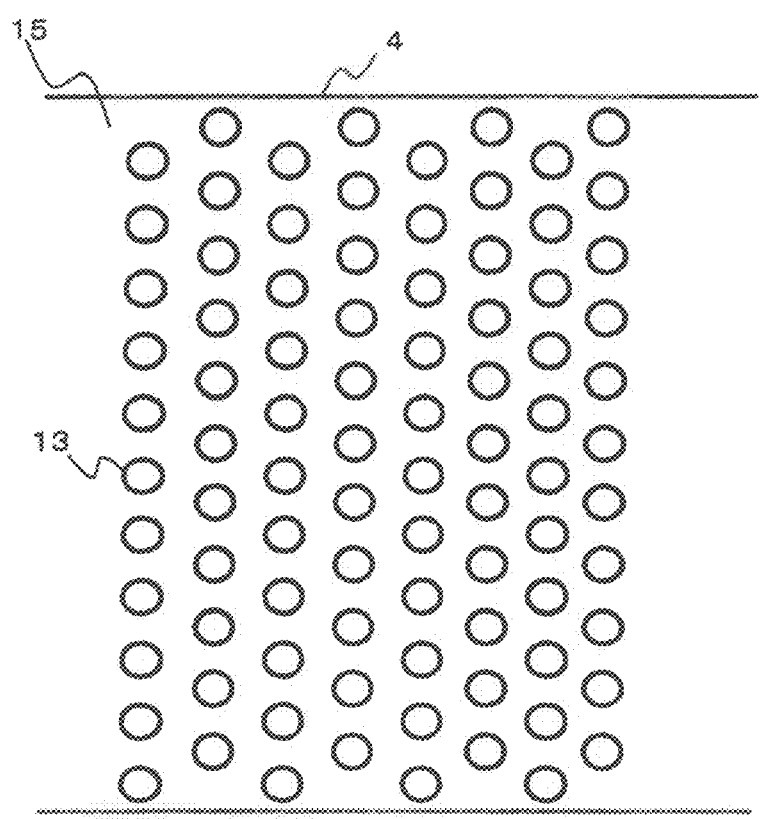
FIG. 4 is an explanatory diagram illustrating exemplary arrangement of point light sources in the first light source.

FIG. 4 is an explanatory diagram illustrating exemplary arrangement of the point light sources 13 in the first light source 4. As illustrated in FIG. 4, for example, the respective point light sources 13 are arranged so as to be aligned in rows on the lateral wall 15 of the first light source 4. Moreover, the respective point light sources 13 are arranged so that the positions of the point light sources in the adjacent rows are deviated from each other. In other words, the plurality of point light sources 13 are aligned in rows and arranged in a staggered configuration. The deviations of the positions of the point light sources in the adjacent rows also can improve the diversity of directions of light incident on the transparent body 17 and traveling through the transparent body 17. FIG. 4 illustrates the arrangement of the point light sources by way of example, and the arrangement of the point light sources is not limited to the mode illustrated in FIG. 4; however, in order to improve the diversity of directions of light, the point light sources are preferably arranged in the mode illustrated in FIG. 4.

Figure 5:
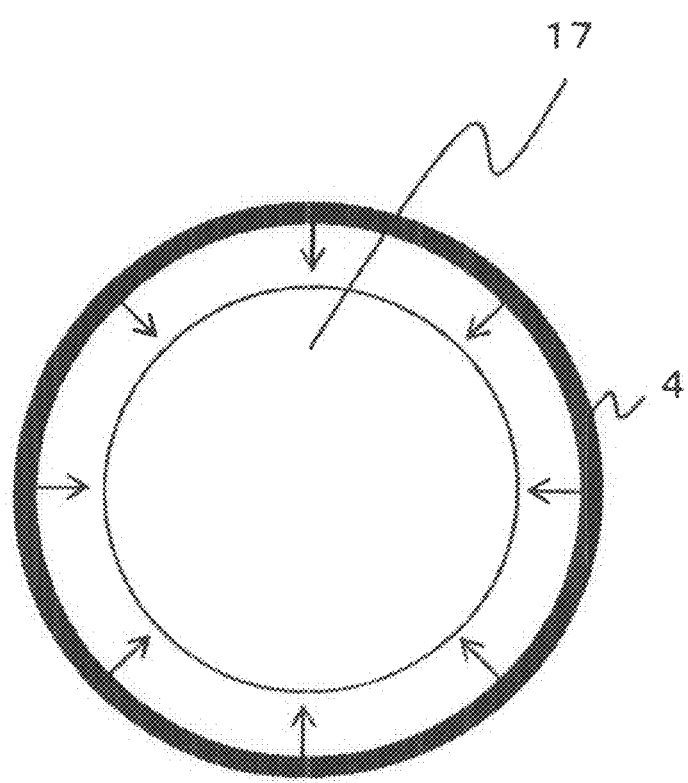
FIG. 5 is a top view illustrating an example of the first light source surrounding a transparent body.

Besides, although the case where the first light source 4 is located only to the left of the transparent body 17 is illustrated in the example provided in FIG. 1, the first light source 4 may be formed to surround the transparent body 17. FIG. 5 is a top view illustrating an example of the first light source 4 surrounding the transparent body 17. In the example illustrated in FIG. 5, the transparent body 17 is a circular cylinder, and its upper face is illustrated. Or more specifically, FIG. 5 provides the top view of the first light source 4 surrounding the entire lateral surface of the circular cylindrical transparent body 17. As illustrated in FIG. 5, the first light source 4 surrounds the transparent body 17 and applies light in each direction, thereby allowing the intensity of light inside the transparent body 17 to be uniformized.

The second light source 5 illustrated in FIG. 1 applies light to the transparent body 17 from a position located opposite to the image capturing unit 2, with the transparent body 17 sandwiched between the image capturing unit 2 and the second light source 5. When the image capturing unit 2 is located above the upper surface of the transparent body 17 as illustrated in FIG. 1 and captures an image of the transparent body 17 from a vertical position with respect to the upper surface thereof, the second light source 5 applies light to the transparent body 17 from below. Since the support unit 1 is transparent, the light applied from the second light source 5 is passed through the support unit 1 and incident on the transparent body 17.

The second light source 5 applies polarized light to the transparent body 17 uniformly. As illustrated in FIG. 1, for example, the second light source 5 includes: an application unit 6 for applying light; and a polarizing plate 7 provided at a position toward which light is applied from the application unit 6, and is formed so that the light applied from the application unit 6 is changed into polarized light through the polarizing plate 7.

The first embodiment is described based on an example in which the respective point light sources 13 of the first light source 4 and the application unit 6 of the second light source 5 each apply white light, and the image capturing unit 2 is a black and white camera for generating a gray scale image.

Hereinafter, the polarizing plate 7 included in the second light source 5 will be referred to as a light source side polarizing plate 7, and the polarizing plate 8 provided adjacent to the image capturing unit 2 will be referred to as an image capture side polarizing plate 8, thus distinguishing the two polarizing plates 7 and 8 from each other.

The image capture side polarizing plate 8 serves as a polarizing plate for blocking polarized light, applied from the second light source 5 and traveling toward the image capturing unit 2, when no transparent body 17 is placed or no polarization cancellation defect exists in the transparent body 17. The polarizing plate driving unit 10 is a driving device for changing the positional state of the image capture side polarizing plate 8. As mentioned above, when no transparent body 17 is placed or no polarization cancellation defect exists in the transparent body 17, the image capture side polarizing plate 8 blocks polarized light applied from the second light source 5; however, when the positional state of the image capture side polarizing plate 8 is changed by the polarizing plate driving unit 10, the polarized light is not blocked by the image capture side polarizing plate 8 but passed therethrough.

For example, the light source side polarizing plate 7 serves as a linearly polarizing plate for changing light into linearly polarized light. In that case, a linearly polarizing plate may be used as the image capture side polarizing plate 8. Further, when the image capture side polarizing plate 8 is positioned by the polarizing plate driving unit 10 so that the light source side polarizing plate 7 and the image capture side polarizing plate 8 are arranged as crossed Nicols, polarized light applied from the second light source 5 is blocked by the image capture side polarizing plate 8. The crossed Nicols arrangement unit a state in which the polarization axis of one of the polarizing plates (i.e., the light source side polarizing plate 7 in this case) and that of the other polarizing plate (i.e., the image capture side polarizing plate 8 in this case) are orthogonal to each other. Note that in this state, the image capture side polarizing plate 8 is positioned in front of the image capturing unit 2 by the polarizing plate driving unit 10, thus blocking polarized light traveling toward the image capturing unit 2. Furthermore, the polarizing plate driving unit 10 changes the position of the image capture side polarizing plate 8 from a state in which the polarized light traveling toward the image capturing unit 2 is blocked by the image capture side polarizing plate 8 to a state in which the polarized light traveling toward the image capturing unit 2 is not blocked. For example, the image capture side polarizing plate 8 is moved to a position outside the image capturing range of the image capturing unit 2 in a direction parallel to the upper surface of the transparent body 17. As a result, the image capture side polarizing plate 8 will not be located in front of the image capturing unit 2, and therefore, the polarized light traveling toward the image capturing unit 2 will not be blocked. Alternatively, the polarizing plate driving unit 10 may rotate the image capture side polarizing plate 8 so that the polarization axis of the light source side polarizing plate 7 and that of the image capture side polarizing plate 8 are in parallel with each other. By arranging the polarization axes of the two polarizing plates 7 and 8 in parallel with each other, the polarized light traveling toward the image capturing unit 2 is allowed to pass through the image capture side polarizing plate 8 even when the image capture side polarizing plate 8 is located in front of the image capturing unit 2.

Moreover, the light source side polarizing plate 7 is not limited to a linearly polarizing plate but may be a polarizing plate for changing light into circularly polarized light or elliptically polarized light.

When the light source side polarizing plate 7 is a circularly polarizing plate for changing light into circularly polarized light, a circularly polarizing plate, by which light is changed into oppositely circularly polarized light, may be positioned as the image capture side polarizing plate 8. When the image capture side polarizing plate 8 is positioned in front of the image capturing unit 2 by the polarizing plate driving unit 10, the polarized light traveling toward the image capturing unit 2 is blocked by the image capture side polarizing plate 8, but upon movement of the image capture side polarizing plate 8 to a position outside the range of the image capturing unit 2 by the polarizing plate driving unit 10, the polarized light traveling toward the image capturing unit 2 is not blocked.

On the other hand, when the light source side polarizing plate 7 is an elliptically polarizing plate for changing light into elliptically polarized light, an elliptically polarizing plate, by which light is changed into oppositely elliptically polarized light having an ellipticity equal to that of the elliptically polarized light, may be positioned as the image capture side polarizing plate 8. Also in this case, upon positioning of the image capture side polarizing plate 8 in front of the image capturing unit 2 by the polarizing plate driving unit 10, the polarized light traveling toward the image capturing unit 2 is blocked by the image capture side polarizing plate 8, but upon movement of the image capture side polarizing plate 8 to a position outside the range of the image capturing unit 2 by the polarizing plate driving unit 10, the polarized light traveling toward the image capturing unit 2 is not blocked. The following description will be made based on an example in which each of the polarizing plates 7 and 8 is a linearly polarizing plate.

The switching unit 11 switches states of the polarizing plate driving unit 10, the first light source 4 and the second light source 5 in accordance with each of the following cases: a case where the image capturing unit 2 captures an image for determining existence or nonexistence of a scattering defect (which will hereinafter be referred to as a "scattering determination image"); a case where the image capturing unit 2 captures an image for determining existence or nonexistence of a light-blocking defect (which will hereinafter be referred to as a "light blockage determination image"); and a case where the image capturing unit 2 captures an image for determining existence or nonexistence of a polarization cancellation defect (which will hereinafter be referred to as a "polarization cancellation determination image"). Further, in each of the above-mentioned cases, the switching unit 11 allows the movement control unit 3 to move the image capturing unit 2 in a direction in which the image capturing unit 2 is brought close to the upper surface of the transparent body or in a direction in which the image capturing unit 2 is brought away from the upper surface of the transparent body.

The defect determining unit 12 determines existence or nonexistence of a defect in the transparent body 17 based on whether or not brightness of pixels in the image captured by the image capturing unit 2 is nonuniform. Specifically, when the brightness of pixels in the image is uniform, it is determined that no defect exists, but when the brightness of pixels in the image is nonuniform and there exists a bright region or a dark region with respect to the background of the image, it is determined that a defect exists. An intensity difference between brightness of the background and that of the region representing a defect in the image varies depending on the type of the defect.

Furthermore, when images for checking a single type of a defect are generated, the image capturing unit 2 repeatedly carries out image capture at given time intervals while moving with constant velocity in the direction in which the image capturing unit 2 is brought close to the upper surface of the transparent body 17 or in the direction in which the image capturing unit 2 is brought away from the upper surface of the transparent body 17, thus generating a plurality of images. When a defect is located inside the depth of field of the image capturing unit 2, a difference in brightness intensity is observed in the image. On the other hand, even if no defect is located inside the depth of field, a difference in brightness intensity occurs in the image also when a defect is located in the vicinity of the depth of field. However, when no defect is located inside the depth of field, a contrast, i.e., a difference in intensity, in the image is low. Accordingly, as the depth of field comes close to a defect, the contrast is increased, and the contrast is maximized when the defect is located within the depth of field; moreover, as the depth of field goes away from the defect, the contrast is reduced. When defective capture images, which are images having nonuniform brightness of pixels, are continuous in a plurality of images obtained by carrying out image capture more than once while the image capturing unit 2 is moved in one direction (i.e., the direction in which the image capturing unit 2 is brought close to the upper surface of the transparent body 17 or the direction in which the image capturing unit 2 is brought away from the upper surface of the transparent body 17), the defect determining unit 12 determines that a defect exists within the depth of field at the point in time when the defective capture image having the highest contrast among the defective capture images is captured.

Figure 6:
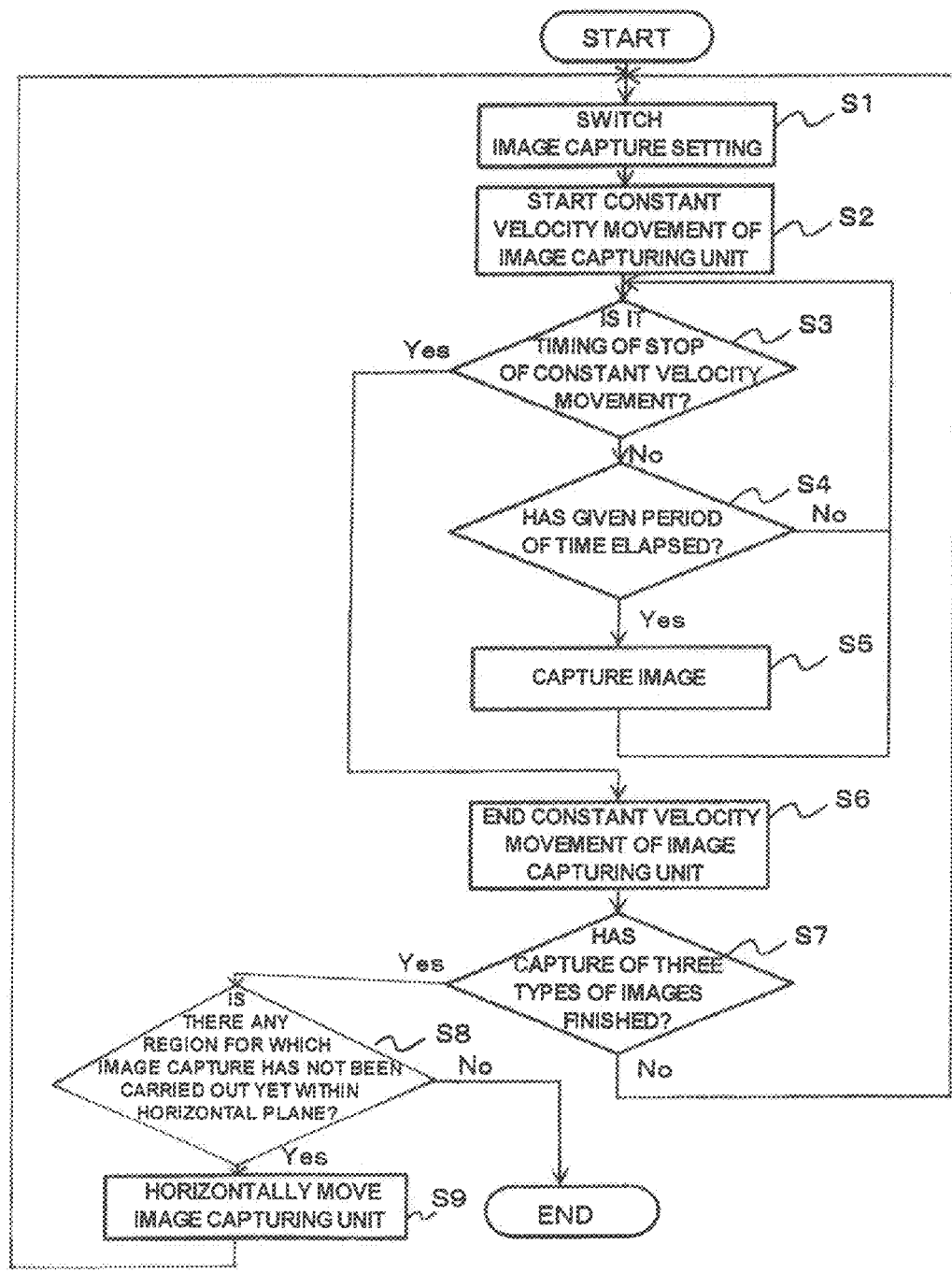
FIG. 6 is a flow chart illustrating examples of operations for capturing images by an image capturing unit.
Figure 7:
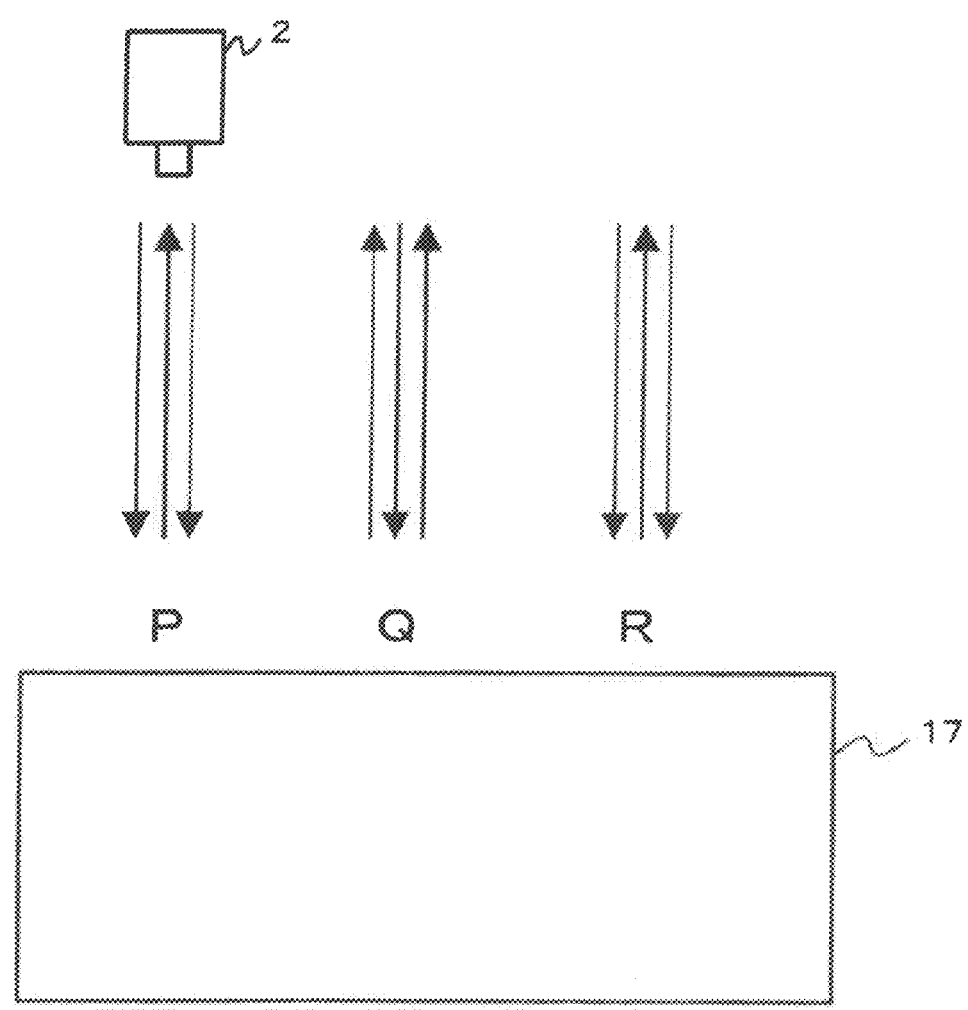
FIG. 7 is an explanatory diagram schematically illustrating motions of the image capturing unit.

Next, operations will be described. FIG. 6 is a flow chart illustrating examples of operations for capturing images by the image capturing unit 2. In addition, FIG. 7 is an explanatory diagram schematically illustrating motions of the image capturing unit 2. In an initial state, the image capturing unit 2 is located at a position which is above a position P at the upper surface of the transparent body 17 illustrated in FIG. 7 and at which an image of the transparent body 17 is captured in a direction perpendicular to the upper surface of the transparent body 17. Further, the description is made based on an example in which the transparent body 17 is placed on the horizontal support unit 1 (see FIG. 1), the upper surface of the transparent body 17 is horizontal, and the image capture driving unit 3 moves the image capturing unit 2 horizontally and vertically with respect to the upper surface of the transparent body 17.

The transparent body 17 serving as an inspection object is put on the support unit 1 in advance. The switching unit 11 switches the setting of each of the polarizing plate driving unit 10, the first light source 4 and the second light source 5 to any one of: scattering determination image capture setting; light blockage determination image capture setting; and polarization cancellation determination image capture setting (Step S1). Note that in this embodiment, the description is made based on an example in which the settings are switched in the following order: the scattering determination image capture setting, the light blockage determination image capture setting, and the polarization cancellation determination image capture setting. Accordingly, when the processing initially goes to Step S1, the light blockage determination image capture setting is made. Furthermore, specific details of the scattering determination image capture setting, the light blockage determination image capture setting and polarization cancellation determination image capture setting will be described later.

After completion of the setting in Step S1, the switching unit 11 allows the image capture driving unit 3 to start constant velocity movement of the image capturing unit 2. In accordance with an instruction from the switching unit 11, the image capture driving unit 3 moves the image capturing unit 2 with constant velocity in a direction in which the image capturing unit 2 is brought close to the upper surface of the transparent body 17 or in a direction in which the image capturing unit 2 is brought away from the upper surface of the transparent body 17 (Step S2). In this embodiment, the description is made based on an example in which the image capturing unit 2 is first moved downward with constant velocity in the position P within a horizontal plane illustrated in FIG. 7.

After the start of the constant velocity movement of the image capturing unit 2, the switching unit 11 determines whether or not the timing of end of the constant velocity movement of the image capturing unit 2 has come (Step S3). For example, the switching unit 11 may determine whether or not the image capturing unit 2 has reached an endpoint of the constant velocity movement thereof.

When the timing of end of the constant velocity movement has not come (No in Step S3), the image capturing unit 2 determines whether or not a given period of time has elapsed from the previous image capture (Step S4). In this step, when image capture has not been carried out yet, the image capturing unit 2 may determine whether or not a given period of time has elapsed from the start of the constant velocity movement. When the given period of time has not elapsed from the previous image capture (or the start of the constant velocity movement when image capture has not been carried out yet), i.e., when the answer is No in Step S4, the process of Step S3 and the subsequent process are repeated. On the other hand, when the given period of time has elapsed from the previous image capture (or the start of the constant velocity movement when image capture has not been carried out yet), i.e., when the answer is Yes in Step S4, the image capturing unit 2 captures an image of the transparent body 17 to generate a capture image thereof (Step S5). In this step, the image capture driving unit 3 does not stop the movement of the image capturing unit 2, and the image capturing unit 2 carries out image capture while moving with constant velocity. When the image capture has been carried out, the image capturing unit 2 outputs, to the defect determining unit 12, the capture image and the position of the image capturing unit 2 at the time of the image capture. After Step S5, the process of Step S3 and the subsequent processes are repeated. By repeating the processes of Steps S3 to S5, the image capturing unit 2 captures images of the inside of the transparent body 17 sequentially while moving with constant velocity, with the states of the first light source 4, the second light source 5 and the image capture side polarizing plate 8 kept unchanged.

Note that although the case where the image capturing unit 2 determines whether or not the given period of time has elapsed (Step S4) has been described in the foregoing example, the determination in Step S4 may be made by the unit other than the image capturing unit 2 (e.g., the switching unit 11 or the image capture driving unit 3), and the image capturing unit 2 may be allowed to carry out image capture upon lapse of the given period of time.

Further, when the timing of end of the constant velocity movement has come (Yes in Step S3), the switching unit 11 allows the image capture driving unit 3 to end the constant velocity movement of the image capturing unit 2. In accordance with an instruction from the switching unit 11, the image capture driving unit 3 stops the constant velocity movement of the image capturing unit 2 (Step S6).

Subsequently, the switching unit 11 determines whether or not image capture has been completed for all the three types of settings (i.e., the scattering determination image capture setting, light blockage determination image capture setting and polarization cancellation determination image capture setting) at the position of the image capturing unit 2 within the horizontal plane (Step S7). When image capture has not been completed for all the three types of settings (No in Step S7), the process of Step S1 and the subsequent processes are repeated. In the present example, image capture has only been carried out with the scattering determination image capture setting with respect to the position P illustrated in FIG. 7, and therefore, the process of Step S1 and the subsequent processes will be repeated.

When the processing goes to Step S1 again, the switching unit 11 switches the setting of each of the polarizing plate driving unit 10, the first light source 4 and the second light source 5 from the scattering determination image capture setting to the light blockage determination image capture setting (Step S1). Then, the process of Step S2 and the subsequent processes are started. However, when the image capturing unit 2 is moved with constant velocity, the image capture driving unit 3 moves the image capturing unit 2 with constant velocity in a direction opposite to that of the previous constant velocity movement. With the previous constant velocity movement, the image capturing unit 2 has been moved downward in the position P (see FIG. 7) and the image capturing unit 2 has been brought close to the upper surface of the transparent body 17; therefore, the image capture driving unit 3 moves the image capturing unit 2 upward with constant velocity in the position P. As for other points, operations of Steps S2 to S6 are similar to those already described above. Until the timing of end of the constant velocity movement comes, the image capturing unit 2 captures images of the inside of the transparent body 17 sequentially while moving with constant velocity. After the timing of end of the constant velocity movement has come and the constant velocity movement of the image capturing unit 2 has been ended (Step S6), the switching unit 11 again determines whether or not image capture has been completed for all the three types of settings (Step S7). In the present example, image capture has not been completed yet with the polarization cancellation determination image capture setting (No in Step S7), and therefore, the process of Step S1 and the subsequent processes will be repeated.

When the process of Step S1 is performed for the third time, the switching unit 11 switches the setting of each of the polarizing plate driving unit 10, the first light source 4 and the second light source 5 from the light blockage determination image capture setting to the polarization cancellation determination image capture setting (Step S1). Then, the process of Step S2 and the subsequent processes are started. With the previous constant velocity movement, the image capturing unit 2 has been moved upward in the position P and the image capturing unit 2 has been brought away from the upper surface of the transparent body 17; therefore, the image capture driving unit 3 moves the image capturing unit 2 downward with constant velocity in the position P. As for other points, operations of Steps S2 to S6 are similar to those already described above. After the timing of end of the constant velocity movement has come and the constant velocity movement of the image capturing unit 2 has been ended (Step S6), the switching unit 11 again determines whether or not image capture has been completed for all the three types of settings (Step S7).

At this point, image capture has been completed for all the three types of settings for the position P (Yes in Step S7), and therefore, the processing goes to Step S8. Thus, before the processing goes to Step S8, the image capturing unit 2 is moved three times, i.e., downward, upward and downward, with constant velocity for the position P illustrated in FIG. 7.

In Step S8, it is determined whether or not there is any region for which image capture has not been carried out yet within the horizontal plane. In other words, it is determined whether or not there is any region which has not entered the image capture range yet within the horizontal plane. When there is no region for which image capture has not been carried out (No Step S8), the processing is brought to an end.

When there is a region for which image capture has not been carried out yet (Yes in Step S8), the switching unit 11 allows the image capture driving unit 3 to horizontally move the image capturing unit 2. For example, the image capturing unit 2 is horizontally moved in the position P illustrated in FIG. 7 to a position Q. In accordance with an instruction from the switching unit 11, the image capture driving unit 3 horizontally moves the image capturing unit 2 (Step S9). In this step, the switching unit 11 allows the image capture driving unit 3 to move the image capturing unit 2 so that the image capture range before the horizontal movement and the image capture range after the horizontal movement partially overlap one another within the horizontal plane. After Step S9, the operations of Step S1 and the subsequent steps are repeated. Specifically, constant velocity movement is repeated three times for the position to which the image capturing unit 2 has been horizontally moved, and scattering determination images, light blockage determination images and polarization cancellation determination images are generated similarly to the case where those images are captured for the position P (see FIG. 7).

Note that the image capturing unit 2 has been moved three times, i.e., downward, upward and downward, with constant velocity for the position P illustrated in FIG. 7; hence, at the position Q after the horizontal movement, the image capturing unit 2 is close to the upper surface of the transparent body 17. Accordingly, scattering determination images, light blockage determination images and polarization cancellation determination images are sequentially obtained by carrying out constant velocity movement three times for the position Q in the following order: upward movement, downward movement and upward movement.

Thereafter, the operations of Steps S1 to S9 are repeated until it is determined in Step S8 that there is no region for which image capture has not been carried out within the horizontal plane. As a result, three types of image groups for the inside of the transparent body 17 are obtained for each image capture region located along the horizontal direction. Besides, each image group includes images that are captured while the depth inside the transparent body 17 is changed at regular intervals.

After the three types of image groups (i.e., a plurality of scattering determination images, a plurality of light blockage determination images and a plurality of polarization cancellation determination images) have been generated for each image capture region, the defect determining unit 12 determines, based on the generated images, existence or nonexistence of each of a scattering defect, a light-blocking defect and a polarization cancellation defect, and determines, when the defect exists, the depth of a position inside the transparent body 17 at which the defect exists.

Hereinafter, details of the specific settings of the polarizing plate driving unit 10, the first light source 4 and the second light source 5 for scattering determination image capture, light blockage determination image capture and polarization cancellation determination image capture will be described, and then a determination operation of the defect determining unit 12 will be described.

When the settings of the polarizing plate driving unit 10, the first light source 4 and the second light source 5 are each switched to the scattering determination image capture setting in Step S1, the switching unit 11 allows the first light source 4 to apply light and allows the second light source 5 to stoplight application. Further, the switching unit 11 allows the polarizing plate driving unit 10 to drive the image capture side polarizing plate 8 so that the image capture side polarizing plate 8 goes out of the image capture range of the image capturing unit 2. Alternatively, the switching unit 11 may allow the polarizing plate driving unit 10 to drive the image capture side polarizing plate 8 so that the image capture side polarizing plate 8 is located in front of the image capturing unit 2 and the polarization axis of the image capture side polarizing plate 8 is parallel to that of the light source side polarizing plate 7.

Figure 8:
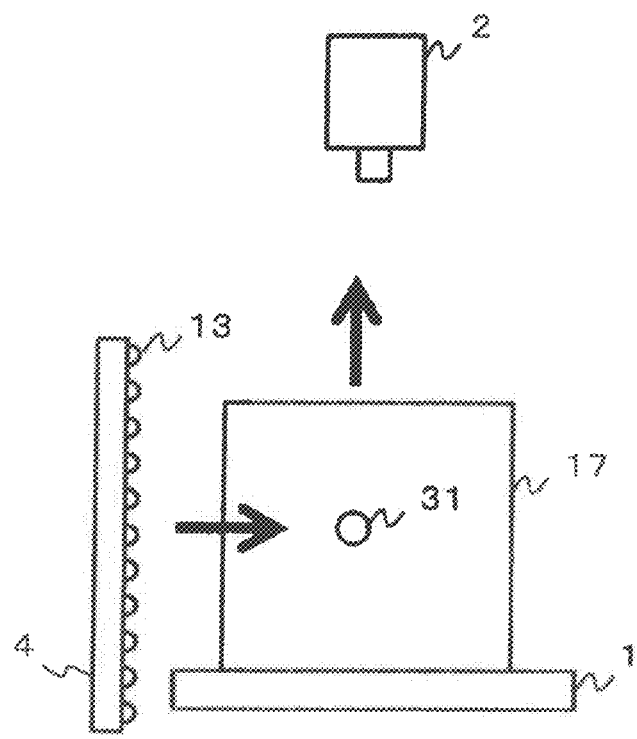
FIG. 8 is an explanatory diagram illustrating a traveling state of light upon existence of a scattering defect when scattering determination image capture setting is made.

FIG. 8 is an explanatory diagram illustrating a traveling state of light upon existence of a scattering defect when the scattering determination image capture setting is made. When light applied from the first light source 4 and incident on the transparent body 17 has reached a spot 31 serving as a scattering defect, the light is scattered in each direction from this spot. As a result, as illustrated in FIG. 8, light traveling from the transparent body 17 toward the image capturing unit 2 is produced. On the other hand, when no scattering defect exists, the light applied from the first light source 4 and incident on the transparent body 17 travels through the transparent body 17 without being scattered, and light traveling toward the image capturing unit 2 will not be produced.

Figure 9A:
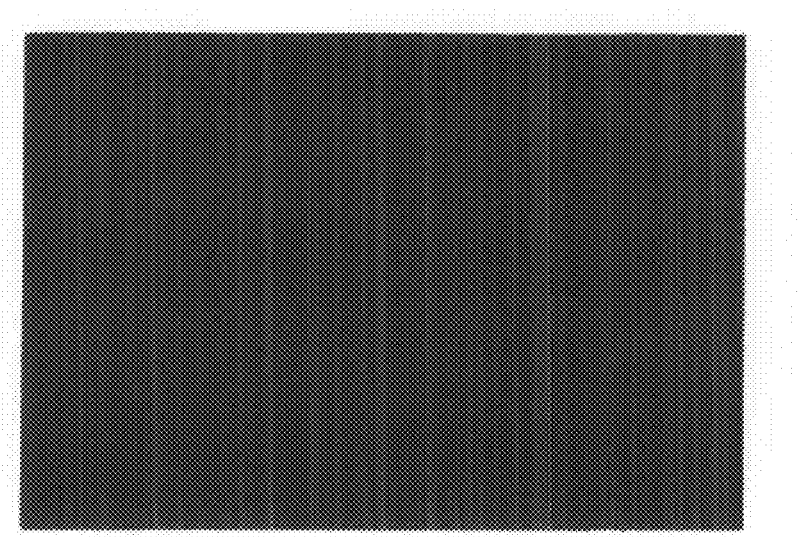
FIG. 9A is an explanatory diagram schematically illustrating an example of a scattering determination image.
Figure 9B:
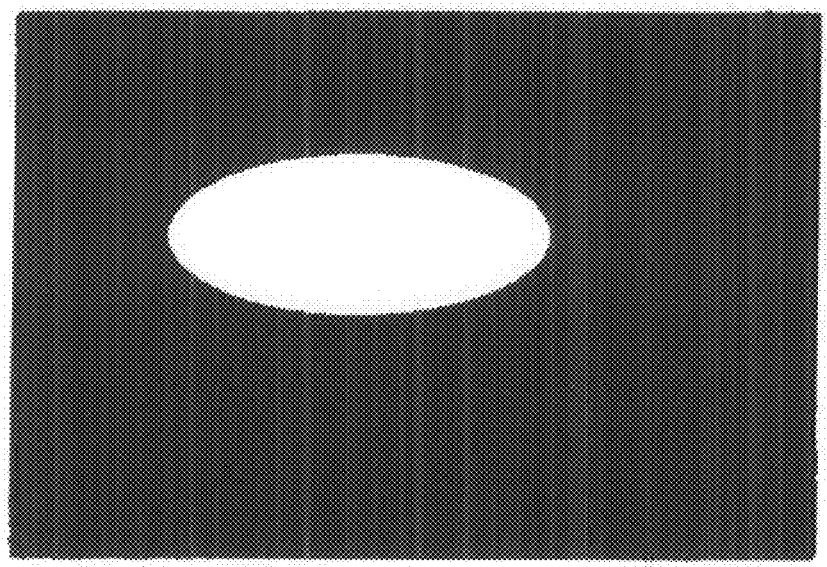
FIG. 9B is an explanatory diagram schematically illustrating an example of a scattering determination image.
Figure 10:
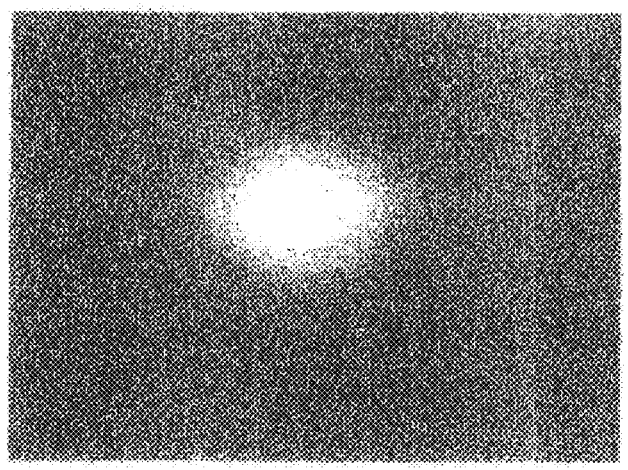
FIG. 10 is an explanatory diagram illustrating an example of a defective capture image having a scattering defect.

FIG. 9A schematically illustrates an image when no scattering defect exists, and FIG. 9B schematically illustrates an image when a scattering defect exists. When no scattering defect exists, light traveling toward the image capturing unit 2 will not be produced, and therefore, the capture image will be a uniformly dark image as illustrated in FIG. 9A. On the other hand, when a scattering defect exists, light traveling toward the image capturing unit 2 is produced by being scattered from the spot where this defect exists, and therefore, the capture image will be a defective capture image in which a bright region is created in the dark background as illustrated in FIG. 9B. FIG. 10 illustrates an example of a defective capture image having a scattering defect.

In addition, at the time of scattering determination image capture, the switching unit 11 may allow the polarizing plate driving unit 10 to drive the image capture side polarizing plate 8 so that the image capture side polarizing plate 8 serves as crossed Nicols with respect to the light source side polarizing plate 7 and is positioned in front of the image capturing unit 2. Even when the image capture side polarizing plate 8 is positioned in this manner, scattered light passes through the image capture side polarizing plate 8, and therefore, the image capturing unit 2 can capture an image of light produced by scattering. Note that at the time of scattering determination image capture, it is sufficient to capture an image indicative of existence or nonexistence of light applied from the first light source 4 and traveling toward the image capturing unit 2 due to scattering. Accordingly, when the polarizing plates 7 and 8 are arranged as crossed Nicols as mentioned above, not only the first light source 4 but also the second light source 5 may be allowed to apply light. However, when a polarization cancellation defect exists, light applied from the second light source 5 reaches the image capturing unit 2, and therefore, the application of light from the second light source 5 is preferably stopped.

When the settings of the polarizing plate driving unit 10, the first light source 4 and the second light source 5 are each switched to the light blockage determination image capture setting in Step S1, the switching unit 11 allows the first light source 4 to stop light application and allows the second light source 5 to apply light. Further, the switching unit 11 allows the polarizing plate driving unit 10 to drive the image capture side polarizing plate 8 so that the image capture side polarizing plate 8 goes out of the image capture range of the image capturing unit 2. Alternatively, the switching unit 11 may allow the polarizing plate driving unit 10 to drive the image capture side polarizing plate 8 so that the image capture side polarizing plate 8 is located in front of the image capturing unit 2 and the polarization axis of the image capture side polarizing plate 8 is parallel to that of the light source side polarizing plate 7.

FIG. 11 is an explanatory diagram illustrating a traveling state of light upon existence of a light-blocking defect when light blockage determination image capture setting is made. When light applied from the second light source 5 and incident on the transparent body 17 has reached a spot 32 serving as a light-blocking defect, the light is blocked at this spot (see FIG. 11), so that the light will not reach the image capturing unit 2. On the other hand, when no light-blocking defect exists, the light applied from the second light source 5 and incident on the transparent body 17 passes through the transparent body 17 without being blocked, and reaches the image capturing unit 2.

Figure 12A:
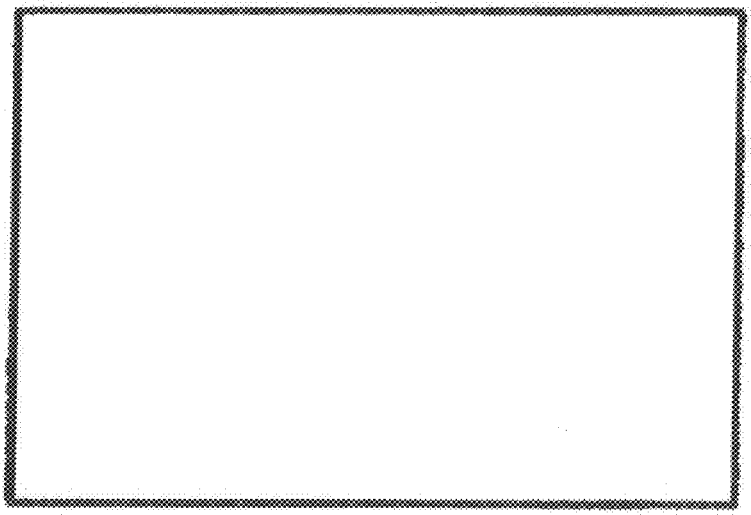
FIG. 12A is an explanatory diagram schematically illustrating an example of a light blockage determination image.
Figure 12B:
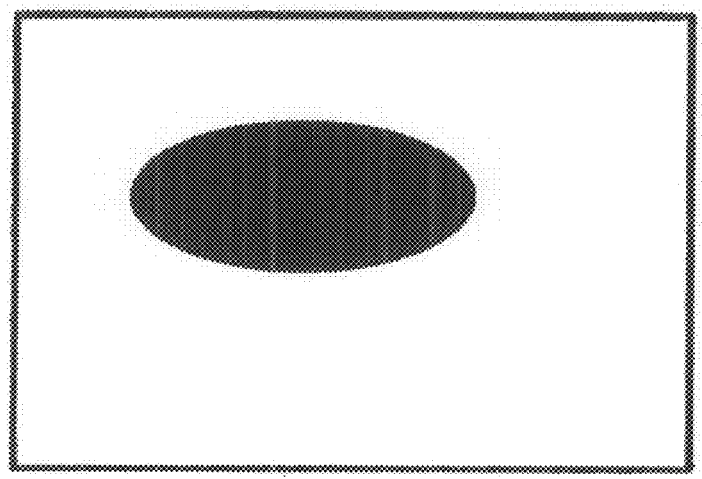
FIG. 12B is an explanatory diagram schematically illustrating an example of a light blockage determination image.
Figure 13:
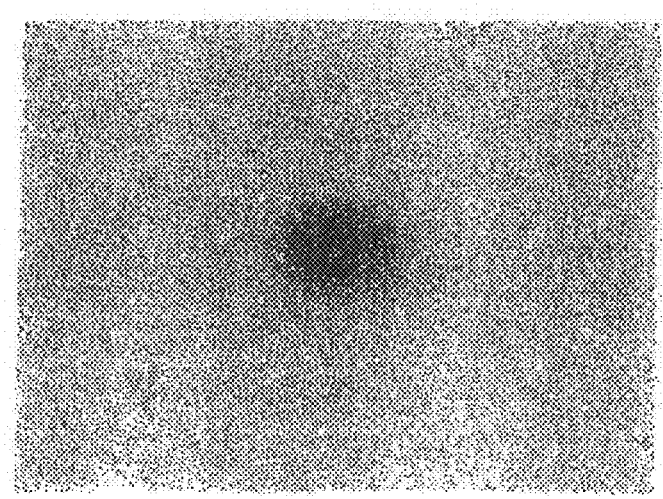
FIG. 13 is an explanatory diagram illustrating an example of a defective capture image having a light-blocking defect.

FIG. 12A schematically illustrates an image when no light-blocking defect exists, and FIG. 12B schematically illustrates an image when a light-blocking defect exists. When no light-blocking defect exists, the light applied from the second light source 5 reaches the image capturing unit 2, and therefore, the capture image will be a uniformly bright image as illustrated in FIG. 12A. On the other hand, when a light-blocking defect exists, the light is blocked at the spot where this defect exists, and therefore, the capture image will be a defective capture image in which a dark region is created in the bright background as illustrated in FIG. 12B. FIG. 13 illustrates an example of a defective capture image having a light-blocking defect.

When the settings of the polarizing plate driving unit 10, the first light source 4 and the second light source 5 are each switched to the polarization cancellation determination image capture setting in Step S1, the switching unit 11 allows the first light source 4 to stop light application and allows the second light source 5 to apply polarized light. Further, the switching unit 11 allows the polarizing plate driving unit 10 to drive the image capture side polarizing plate 8 so that the image capture side polarizing plate 8 serves as crossed Nicols with respect to the light source side polarizing plate 7 and is positioned in front of the image capturing unit 2.

Figure 14:
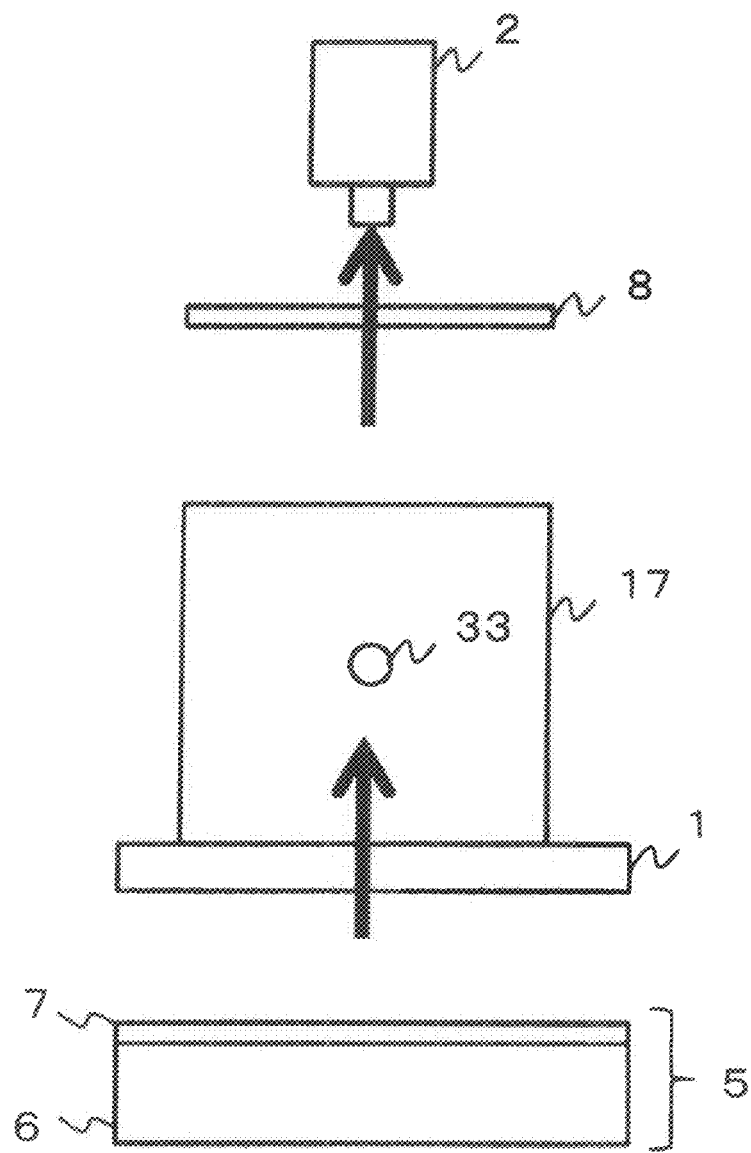
FIG. 14 is an explanatory diagram illustrating a traveling state of light upon existence of a polarization cancellation defect when polarization cancellation determination image capture setting is made.

FIG. 14 is an explanatory diagram illustrating a traveling state of light upon existence of a polarization cancellation defect when polarization cancellation determination image capture setting is made. When no polarization cancellation defect exists, the polarized light applied from the second light source 5 and incident on the transparent body 17 passes through the transparent body 17 without any change in polarized state, and is blocked by the image capture side polarizing plate 8. On the other hand, when a spot 33 serving as a polarization cancellation defect exists, the polarized light applied from the second light source 5 and incident on the transparent body 17 is changed in the polarized state at this spot, and passes through the transparent body 17. The light whose polarized state is changed by the polarization cancellation defect will not be blocked by the image capture side polarizing plate 8, and reaches the image capturing unit 2.

Figure 15:
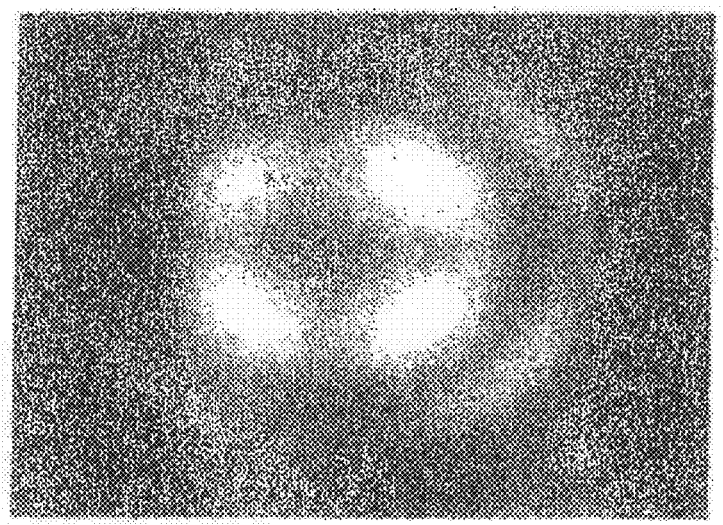
FIG. 15 is an explanatory diagram illustrating an example of a defective capture image having a polarization cancellation defect.

As described above, when no polarization cancellation defect exists, the polarized light applied from the second light source 5 is blocked, and therefore, the image captured when no polarization cancellation defect exists will be a uniformly dark image similarly to the case illustrated in FIG. 9A. On the other hand, when a polarization cancellation defect exists, the polarized light passes through the image capture side polarizing plate 8 and reaches the image capturing unit 2, and therefore, the capture image will be a defective capture image in which a bright region is created in the dark background similarly to the case illustrated in FIG. 9B. FIG. 15 illustrates an example of a defective capture image having a polarization cancellation defect.

The defect determining unit 12 determines existence or nonexistence of a scattering defect by using a scattering determination image. The defect determining unit 12 makes comparisons on brightness of respective pixels of a scattering determination image, and when the brightness of the respective pixels is uniformly low (e.g., when the brightness of the respective pixels is lower than a predetermined scattering determination threshold value), it is determined that no scattering defect exists within the depth of field at the time of capture of this image. Further, the defect determining unit 12 makes comparisons on brightness of respective pixels of a scattering determination image, and when the brightness of part of the pixels included in the respective pixels of the scattering determination image is higher than that of the surrounding pixels, it is determined that a scattering defect exists. For example, when the brightness of part of the pixels is equal to or higher than the scattering determination threshold value and the brightness of the surrounding pixels is lower than the scattering determination threshold value, it is determined that a scattering defect exists. Furthermore, it is determined that the scattering defect exists within the depth of field at the time of capture of this defective capture image.

However, when such defective capture images are continuous, the defect determining unit 12 determines that a scattering defect exists within the depth of field at the time of capture of the defective capture image having the highest contrast among the continuous defective capture images, and that no scattering defect exists within the depth of field at the time of capture of the other defective capture images.

Moreover, the defect determining unit 12 determines existence or nonexistence of a light-blocking defect by using a light blockage determination image. The defect determining unit 12 makes comparisons on brightness of respective pixels of a light blockage determination image, and when the brightness of the respective pixels is uniformly high (e.g., when the brightness of the respective pixels is higher than a predetermined light blockage determination threshold value), it is determined that no light-blocking defect exists within the depth of field at the time of capture of this image. Further, the defect determining unit 12 makes comparisons on brightness of respective pixels of a light blockage determination image, and when the brightness of part of the pixels included in the respective pixels of the light blockage determination image is lower than that of the surrounding pixels, it is determined that a light-blocking defect exists. For example, when the brightness of part of the pixels is equal to or lower than the light blockage determination threshold value and the brightness of the surrounding pixels is higher than the light blockage determination threshold value, it is determined that a light-blocking defect exists. Furthermore, it is determined that the light-blocking defect exists within the depth of field at the time of capture of this defective capture image.

However, when such defective capture images are continuous, the defect determining unit 12 determines that a light-blocking defect exists within the depth of field at the time of capture of the defective capture image having the highest contrast among the continuous defective capture images, and that no light-blocking defect exists within the depth of field at the time of capture of the other defective capture images.

Besides, the defect determining unit 12 determines existence or nonexistence of a polarization cancellation defect by using a polarization cancellation determination image. The defect determining unit 12 makes comparisons on brightness of respective pixels of a polarization cancellation determination image, and when the brightness of the respective pixels is uniformly low (e.g., when the brightness of the respective pixels is lower than a predetermined polarization cancellation determination threshold value), it is determined that no polarization cancellation defect exists within the depth of field at the time of capture of this image. Further, the defect determining unit 12 makes comparisons on brightness of respective pixels of a polarization cancellation determination image, and when the brightness of part of the pixels included in each polarization cancellation determination image is higher than that of the surrounding pixels, it is determined that a polarization cancellation defect exists. For example, when the brightness of part of the pixels is equal to or higher than the polarization cancellation determination threshold value and the brightness of the surrounding pixels is lower than the polarization cancellation determination threshold value, it is determined that a polarization cancellation defect exists.

However, when such defective capture images are continuous, the defect determining unit 12 determines that a polarization cancellation defect exists within the depth of field at the time of capture of the defective capture image having the highest contrast among the continuous defective capture images, and that no polarization cancellation defect exists within the depth of field at the time of capture of the other defective capture images.

For any of these defects, the depth of a position at which the defect exists can be suitably determined by identifying the defective capture image having the highest contrast as described above. Note that the position of the depth of field at the time of capture of a defective capture image may be obtained from the position of the image capturing unit 2 at the time of the image capture, for example.

The effects of the first embodiment will be described.

According to the first embodiment, the image capture driving unit 3 moves the image capturing unit 2 in a direction in which the image capturing unit 2 is brought close to the upper surface of the transparent body 17 and in a direction in which the image capturing unit 2 is brought away from the upper surface of the transparent body 17, and the image capturing unit 2 captures a plurality of images of the transparent body 17 during the movement thereof. Hence, the images are captured while the position of the depth of field of the image capturing unit is adjusted to a plurality of spots inside the transparent body 17. Then, when brightness of pixels in the captured image is nonuniform, the defect determining unit 12 determines that a defect exists within the depth of field at the time of capture of this image. Accordingly, the depth of a position inside the transparent body 17 at which the defect exists can be determined.

Further, when defective capture images in which brightness of pixels is nonuniform are continuous in a plurality of images captured by the image capturing unit 2 while it is moved in one direction, the defect determining unit 12 determines that a defect exists within the depth of field at the time of capture of the defective capture image having the highest contrast among the defective capture images. Accordingly, the position of a defect inside the transparent body 17 can be more accurately determined.

Furthermore, the image capture driving unit 3 moves the image capturing unit 2 with constant velocity, and the image capturing unit 2 captures images of the transparent body 17 while moving with constant velocity. Accordingly, the time required to move the image capturing unit 2 can be reduced, and the time required to obtain all images can be reduced. As a result, cycle time can be reduced. If the image capturing unit 2 is stopped for each image capture, it takes time to complete image capture accordingly, but such an increase in the time can be prevented in the first embodiment. Moreover, it is conceivable that the velocity of the image capturing unit 2 may be reduced each time image capture is carried out and may be increased after the image capture; however, in that case, the image capturing unit 2 is accelerated each time image capture is carried out. Then, since acceleration at the time of image capture is not necessarily kept constant, an image capture condition will be changed upon change of the acceleration. In the present embodiment, the image capturing unit 2 carries out image capture during its constant velocity movement, and therefore, the image capture condition (acceleration) can be kept unchanged.

In addition, in the first light source 4, the height of the lateral wall 15 (see FIG. 3) on which the point light sources 13 are arranged is higher than that of the transparent body 17. Besides, the point light source $13_a$ (see FIG. 3) at the end portion close to the image capturing unit 2 is located at a position higher than that of the surface of the transparent body 17, which faces toward the image capturing unit 2, and the point light source $13_b$ (see FIG. 3) at the end portion away from the image capturing unit 2 is located at a position lower than that of the surface of the transparent body 17, which is opposite to the image capturing unit 2. Accordingly, the direction of light traveling through the transparent body 17 can be diversified. Moreover, even at a position located in the vicinity of the upper surface or bottom surface of the transparent body 17, the traveling direction of light can be diversified. Some of defects might not cause scattering when light is incident from a particular direction. For example, such defects include a scattering defect that does not scatter light incident from a horizontal direction but scatters light incident from other directions. Even such a defect can be detected with high sensitivity by diversifying the direction of light traveling through the transparent body 17. In addition, even when such a defect exists in the vicinity of the upper surface or bottom surface of the transparent body 17, the defect can be detected with high sensitivity. Note that referring to FIG. 3, when the height of the lateral wall 15 is excessively higher than that of the transparent body 17, normal reflection of light, applied from the upper point light sources arranged on the lateral wall 15, might occur at the upper surface of the transparent body 17, and reflected light might reach the image capturing unit 2, thereby causing trouble in defect detection. Accordingly, the height of the lateral wall 15 is preferably set at a level equal to or lower than a height by which light applied from the uppermost point light source located on the lateral wall 15 will not reach the image capturing unit 2 even when normal reflection of the light has occurred at the upper surface of the transparent body 17.

Further, the point light sources of the first light source 4 are aligned in rows and arranged so that the positions of the point light sources in the adjacent rows are deviated from each other. As a result, the diversity of directions of light traveling through the transparent body 17 can be improved, and defect detection accuracy can be further increased.

Furthermore, in the first embodiment, there are provided the first light source 4 located laterally of the position of the transparent body 17, and the second light source 5 located below the position of the transparent body 17. Moreover, the defect determining unit 12 determines whether or not brightness of pixels in an image captured in a state in which light is applied to the transparent body 17 by the first light source 4 is nonuniform, and also determines whether or not brightness of pixels in an image captured in a state in which light is applied to the transparent body 17 by the second light source 5 is nonuniform, thus making it possible to perform inspection for a plurality of types of defects. Hence, inspection for a plurality of defects can be performed by using a single apparatus without having to prepare an inspection apparatus for each type of a defect and transfer a transparent body to another inspection apparatus.

In the first embodiment, the switching unit 11 makes the scattering determination image capture setting, light blockage determination image capture setting and polarization cancellation determination image capture setting, thus making it possible to perform inspection for the three types of defects, i.e., scattering defect, light-blocking defect and non-refraction defect, by using a single apparatus.

Figure 16:
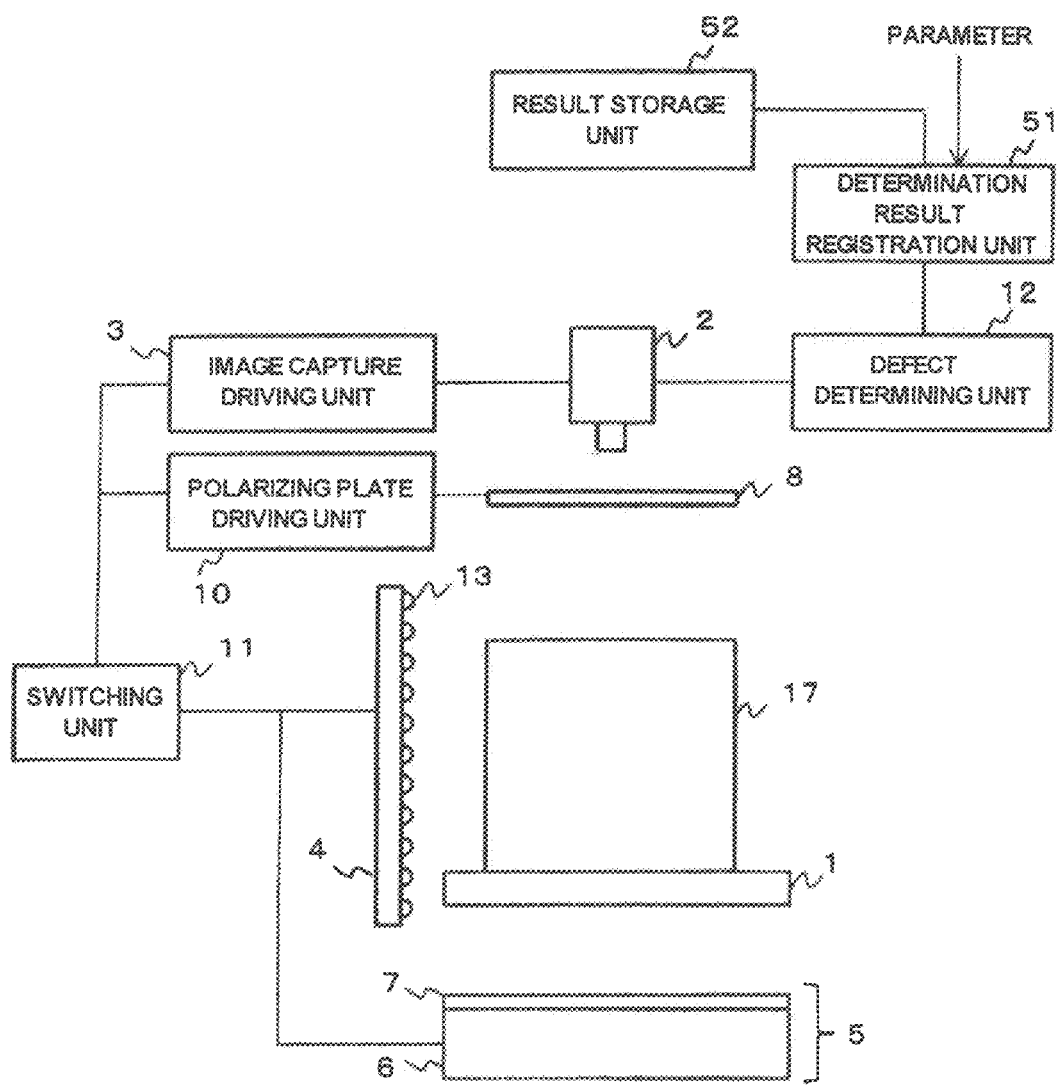
FIG. 16 is a block diagram illustrating a variation of the first embodiment.

Next, a variation of the first embodiment will be described. FIG. 16 is a block diagram illustrating the variation of the first embodiment. Constituent elements similar to those illustrated in FIG. 1 are identified by the same reference characters as those used in FIG. 1, and description thereof will be omitted. In addition to the constituent elements illustrated in FIG. 1, a transparent body inspecting device of the present variation includes: a determination result registration unit 51; and a result storage unit 52.

The result storage unit 52 is a storage device for storing: a parameter such as a production condition for the transparent body 17 serving as an inspection object; and a determination result obtained by the defect determining unit 12. A determination result obtained by the defect determining unit 12 indicates the type of a defect and its position detected by the defect determining unit 12.

A parameter such as a production condition for the transparent body 17 serving as an inspection object is inputted to the determination defect registration unit 51 from an operator of the transparent body inspecting device, for example. Examples of the parameter such as a production condition for the transparent body 17 include setting of an apparatus by which the transparent body 17 is produced; and an environmental condition thereof, but the type of the parameter is not limited thereto. When the parameter has been inputted and the determination result has been derived by the defect determining unit 12, the determination defect registration unit 51 allows the result storage unit 52 to store the parameter and the determination result (indicative of the type of the detected defect and its position) in such a manner that the parameter and the determination result are associated with each other.

Consequently, a collection of pieces of information including parameters and inspection results can be accumulated in the result storage unit 52. Using the collection of pieces of information as a database, the operator can analyze, for example, the association among the type of the parameter, the type of the defect and the position of occurrence of the defect, and can feed back the analysis result to a production process of the transparent body.

Further, using the result stored in the result storage unit 52, the operator can determine whether the transparent body 17 serving as an inspection object should be transferred to a next step or should be transferred to a step for excluding a defective region.

Next, another variation of the first embodiment will be described. The defect determining unit 12 may detect a foreign substance (e.g., minute dirt or the like) existing at the upper surface of the transparent body 17 in such a manner that the foreign substance is distinguished from a defect. Specifically, when images in which brightness of pixels is nonuniform are continuous in a plurality of images obtained by carrying out image capture more than once while the image capturing unit 2 is moved in one direction and the contrast of the images is monotonously reduced or monotonously increased, the defect determining unit 12 may determine that a foreign substance exists at the upper surface of the transparent body 17 instead of determining that a defect exists inside the transparent body 17. Furthermore, when the contrast is temporarily increased and is then reduced, the defect determining unit 12 may determine that a defect exists within the depth of field at the time of capture of the image having the highest contrast among the continuous images, in which brightness of pixels is nonuniform, as already explained above.

Also in an image captured in a state in which a foreign substance existing at the upper surface of the transparent body 17 is located within the depth of field, brightness is nonuniform. Moreover, also when the depth of field has been moved to the inside of the transparent body 17, the brightness of the captured image might be nonuniform due to the influence of the foreign substance. However, the contrast is higher in the state in which the foreign substance is located within the depth of field. In addition, an image captured in a state in which the depth of field is located at a position higher than that of the upper surface of the transparent body 17 is excluded from objects for which existence or nonexistence of a defect is determined. Accordingly, when a foreign substance exists at the upper surface of the transparent body 17, the contrast of an image, resulting from this foreign substance, is maximized in the state in which the foreign substance is located within the depth of field. Hence, when images in which brightness of pixels is nonuniform are continuously obtained due to the foreign substance existing at the upper surface of the transparent body 17, the contrast of the continuous images is monotonously reduced or monotonously increased. Specifically, when the image capturing unit 2 captures images while moving downward, the contrast is monotonously reduced, and when the image capturing unit 2 captures images while moving upward, the contrast is monotonously increased. Accordingly, when images in which brightness of pixels is nonuniform are continuous, the defect determining unit 12 can determine, based on monotonous reduction or monotonous increase in the contrast of the images, that a foreign substance exists at the upper surface of the transparent body 17 instead of determining that a defect exists inside the transparent body 17.

Alternatively, the defect determining unit 12 may detect a foreign substance existing at the upper surface of the transparent body 17 by using the other method. For example, the transparent body inspecting device stores a plurality of captured images of a defect existing inside the transparent body 17, and a plurality of captured images of a foreign substance existing at the upper surface of the transparent body, or stores, on an image-by-image basis, feature amounts of a plurality of captured images of a defect existing inside the transparent body, and feature amounts of a plurality of captured images of a foreign substance existing at the upper surface of the transparent body. These images or image feature amounts may be prepared in advance and stored in a storage device (not illustrated) of the transparent body inspecting device. Then, when brightness of an image captured in Step S5 (see FIG. 6) is nonuniform, the defect determining unit 12 may compare the captured image with a defect image and a foreign substance image which are prepared in advance, thus determining which of the probability of correspondence of the captured image to the defect image and the probability of correspondence of the captured image to the foreign substance image is higher. Alternatively, the defect determining unit 12 may compare the feature amount of the captured image with that of the defect image and that of the foreign substance image which are prepared in advance, thus making the foregoing determination. When it is determined that the probability of correspondence of the captured image to the defect image is higher than that of correspondence of the captured image to the foreign substance image, the defect determining unit 12 may determine that a defect exists within the depth of field at the time of capture of the captured image. On the other hand, when it is determined that the probability of correspondence of the captured image to the foreign substance image is higher than that of correspondence of the captured image to the defect image, the defect determining unit 12 may determine that a foreign substance exists at the upper surface of the transparent body 17. Note that when images having nonuniform brightness of pixels are continuously obtained, the defect determining unit 12 may compare the image having the highest contrast with the defect image and foreign substance image which are prepared in advance. Moreover, a method for determining to which of the prepared defect image and foreign substance image the captured image corresponds is not limited to any particular method. For example, a method disclosed in WO 2008/004559 may be used to determine to which of the defect image and foreign substance image the captured image corresponds.

Figure 17:
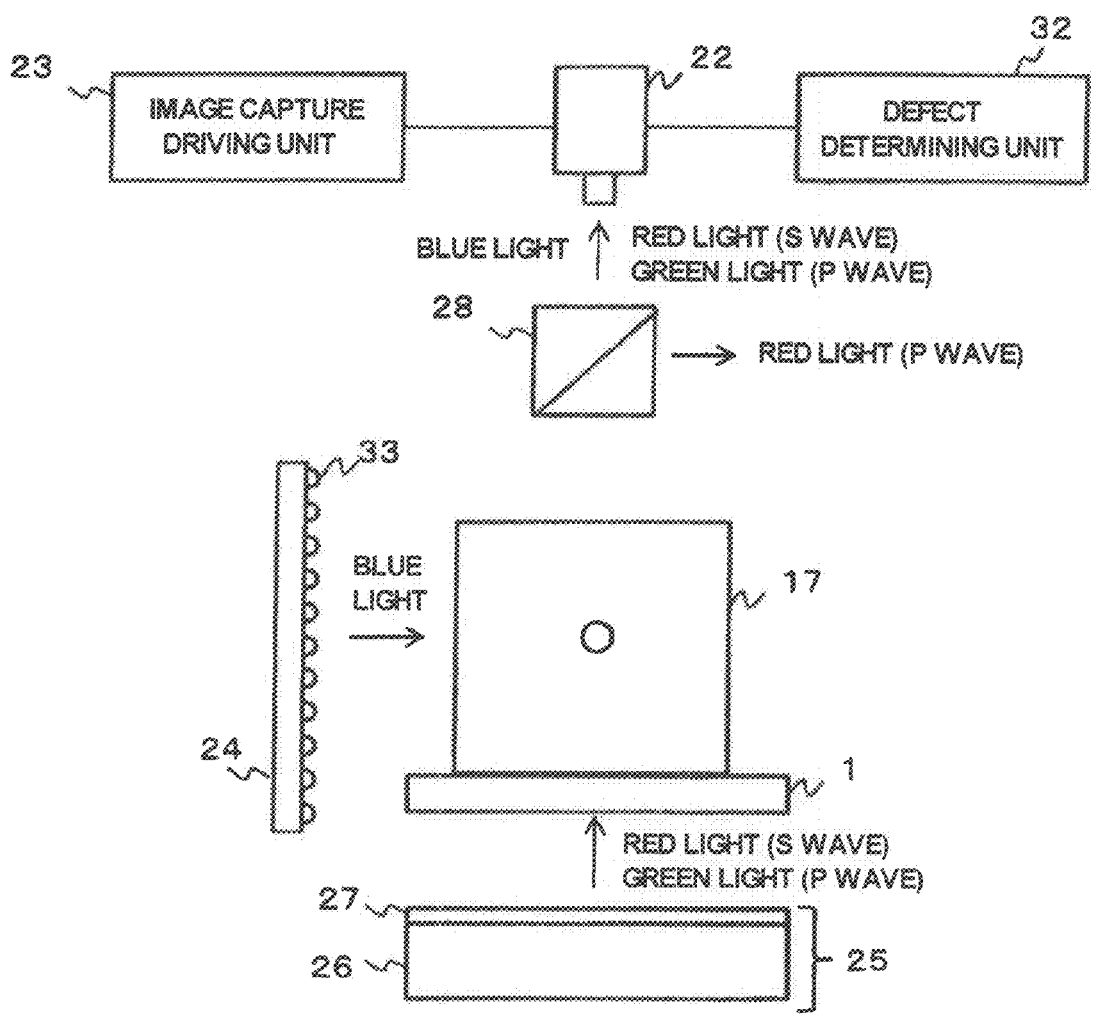
FIG. 17 is a block diagram illustrating an example of a second embodiment according to the present invention.

FIG. 17 is a block diagram illustrating an example of a second embodiment according to the present invention. A transparent body inspecting device according to the second embodiment includes: a support unit 1; an image capturing unit 22; an image capture driving unit 23; a first light source 24; a second light source 25; a polarized light beam splitter 28; and a defect determining unit 32. A transparent body 17 serving as an inspection object is similar to that described in the first embodiment.

Similarly to the first embodiment, the support unit 1 is a transparent support member for supporting the transparent body 17.

Similarly to the image capturing unit 2 in the first embodiment, the image capturing unit 22 is a camera whose depth of field is smaller than the height of the transparent body 17. However, the image capturing unit 22 is the camera for generating a color image.

The image capture driving unit 23 is a driving device for moving the image capturing unit 22, and moves the image capturing unit 22 in a direction in which the image capturing unit 22 is brought close to the upper surface of the transparent body 17 and in a direction in which the image capturing unit 22 is brought away from the upper surface of the transparent body 17. In this case, similarly to the first embodiment, the image capture driving unit 23 allows the image capturing unit 22 to move with constant velocity, and the image capturing unit 2 captures images of the transparent body 17 at given time intervals while moving with constant velocity. Further, the image capture driving unit 23 also moves the image capturing unit 22 horizontally. The image capture driving unit 23 moves the image capturing unit 22 to various positions within a horizontal plane, and moves, from these positions, the image capturing unit 22 with constant velocity in the direction in which the image capturing unit 22 is brought close to the upper surface of the transparent body 17 or in the direction in which the image capturing unit 22 is brought away from the upper surface of the transparent body 17.

The first light source 24 applies light to the transparent body in a direction deviated by 90 degrees with respect to an optical axis direction of the image capturing unit 22. The first light source 24 in the second embodiment applies light of a particular wavelength (hereinafter referred to as a "first wavelength") to the transparent body 17.

Similarly to the first embodiment, the first light source 24 has a lateral wall parallel to the movement directions of the image capturing unit 22 in which the image capturing unit 22 is brought close to the upper surface of the transparent body 17 and in which the image capturing unit 22 is brought away from the upper surface of the transparent body 17. The first light source 24 is provided, at its lateral wall, a plurality of point light sources 33 for applying light of the first wavelength. A positional relationship between the first light source 24 and the transparent body 17 on the support unit 1 is similar to that in the first embodiment. Of the point light sources 33 arranged on the lateral wall, the point light source at an end portion close to the image capturing unit 22 is preferably located at a position higher than that of the surface of the transparent body 17, which faces toward the image capturing unit 22. On the other hand, of the point light sources 33 arranged on the lateral wall, the point light source at an end portion away from the image capturing unit 23 is preferably located at a position lower than that of the surface of the transparent body 17, which is opposite to the image capturing unit 22. Moreover, the point light sources 33 are preferably aligned in rows and arranged so that the positions of the point light sources in the adjacent rows are deviated from each other.

The second light source 25 applies polarized light to the transparent body 17 from a position located opposite to the image capturing unit 22, with the transparent body 17 sandwiched between the image capturing unit 22 and the second light source 25. The second light source 25 in the second embodiment applies P waves of light of two types of wavelengths different from the first wavelength (which will be referred to as a "second wavelength" and a "third wavelength"). For example, the second light source 25 includes: an application unit 26 for applying light of the second wavelength and light of the third wavelength; and a polarizing plate 27 provided at a position toward which light is applied from the application unit 26, and the light of the two types of wavelengths applied from the application unit 26 is changed into P wave light through the polarizing plate 27.

Since light laterally incident on the transparent body 17 is used to determine a scattering defect, the first light source 24 preferably applies, as the light of the first wavelength, short-wavelength light (e.g., light of a wavelength of less than about 550 nm). With the use of the short-wavelength light, a scattering defect can be detected with high accuracy.

In addition, since the light of the second wavelength is used to determine a light-blocking defect, the second light source 25 preferably applies, as the light of the second wavelength, middle-wavelength light (e.g., light of a wavelength of approximately 550 nm). With the use of the middle-wavelength light, a light-blocking defect can be detected with high accuracy. The second light source 25 may apply, as the light of the third wavelength, long-wavelength light whose wavelength is different from the first wavelength and the second wavelength.

Specifically, the first light source 24 may apply blue light as the light of the first wavelength. The second light source 25 may apply green light as the light of the second wavelength, and may apply red light as the light of the third wavelength. The following description will be made based on an example in which the first light source 24 and the second light source 25 apply light in the above-described manner.

However, the wavelengths of the light applied by the first light source 24 and the second light source 25 are not limited to the foregoing wavelengths but may be changed as long as the wavelengths are divided into three types. For example, the first light source 24 may apply green light, and the second light source 25 may apply blue light and red light.

In the present example, blue light from the first light source 24, and P wave of green light and P wave of red light from the second light source 25 are applied simultaneously.

The polarized light beam splitter 28 reflects only a P wave of light of a particular wavelength, and allows light of other wavelengths to be transmitted therethrough. Besides, even in the case of light of the particular wavelength, the polarized light beam splitter 28 allows an S wave to be transmitted therethrough. In this embodiment, the description is made based on an example in which the polarized light beam splitter 28 reflects only the P wave of red light. Accordingly, the S wave of red light, blue light and green light pass through the polarized light beam splitter 28.

Using a color image generated by capturing an image of the transparent body 17 by the image capturing unit 22 in a state in which the light of the three types of wavelengths is simultaneously applied, the defect determining unit 32 performs inspection for each of a scattering defect, a light-blocking defect and a polarization cancellation defect. The defect determining unit 32 determines existence or nonexistence of a scattering defect based on whether or not brightness of pixels (i.e., blue pixels) included in the image and having a color corresponding to the first wavelength is uniform. Similarly, the defect determining unit 32 determines existence or nonexistence of a light-blocking defect based on whether or not brightness of pixels (i.e., green pixels) included in the image and having a color corresponding to the second wavelength is uniform, and determines existence or nonexistence of a polarization cancellation defect based on whether or not brightness of pixels (i.e., red pixels) having a color corresponding to the third wavelength is uniform.

Figure 18:
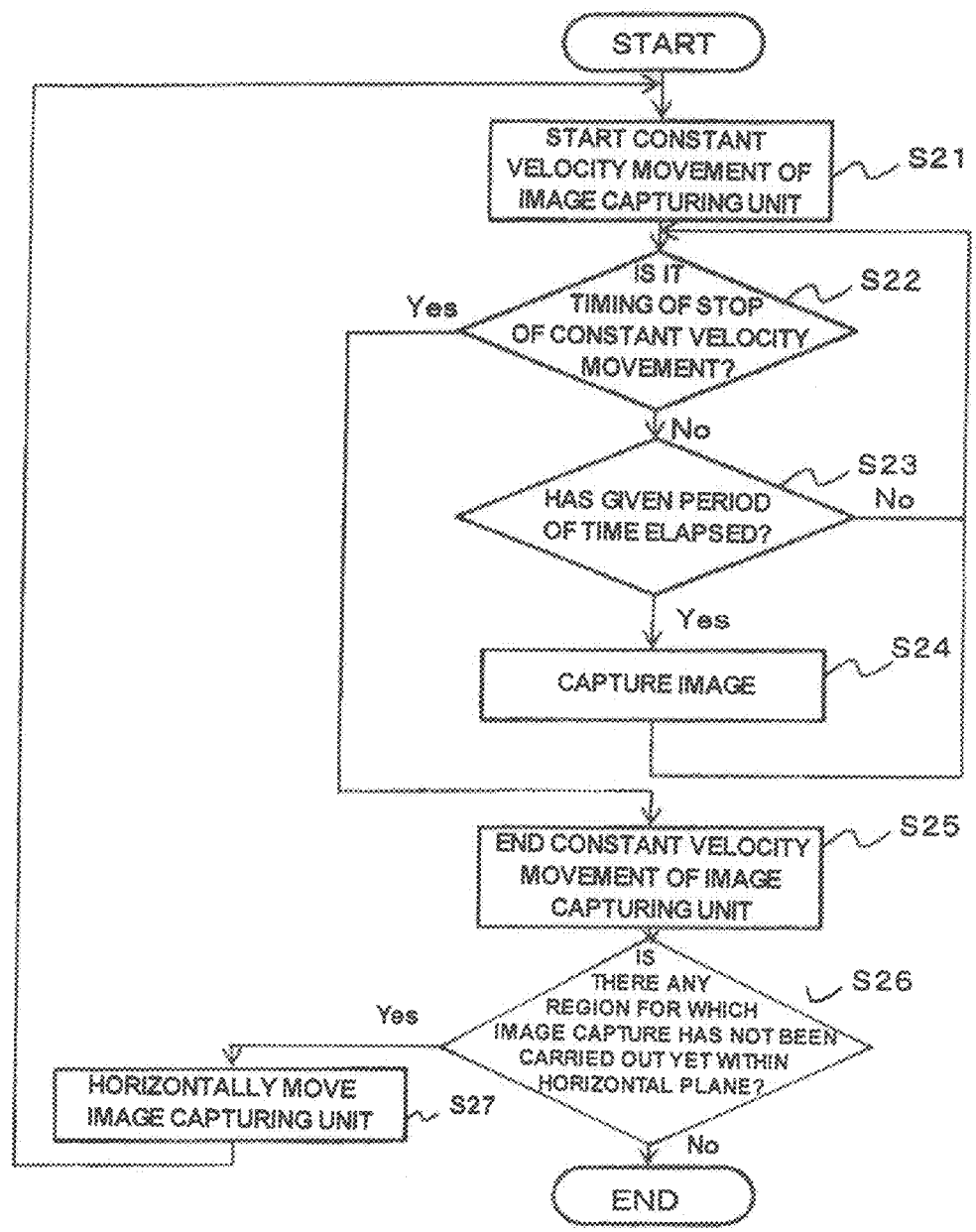
FIG. 18 is a flow chart illustrating examples of operations for capturing images by an image capturing unit.

Next, operations will be described. FIG. 18 is a flowchart illustrating examples of operations for capturing images by the image capturing unit 22. The transparent body 17 serving as an inspection object is put on the support unit 1 in advance. Further, the first light source 24 keeps applying blue light to the transparent body 17. At this time, the second light source 25 simultaneously keeps applying the P wave of green light and the P wave of red light to the transparent body 17. In the second light source 25, the application unit 26 applies green light and red light, and the polarizing plate 27 changes the green light and red light into P waves. As a result, the P wave of green light, the P wave of red light, and blue light are simultaneously applied to the transparent body 17.

In this state, the image capture driving unit 23 allows the image capturing unit 22 to start constant velocity movement (Step S21). The following description is made based on an example in which the image capturing unit 22 is first moved downward with constant velocity.

After the start of the constant velocity movement of the image capturing unit 2, the image capture driving unit 23 determines whether or not the timing of end of the constant velocity movement of the image capturing unit 22 has come (Step S22). For example, the image capture driving unit 23 may determine whether or not the image capturing unit 22 has reached an end point of the constant velocity movement thereof.

When the timing of end of the constant velocity movement has not come (No in Step S22), the image capturing unit 22 captures images of the transparent body 17 at given time intervals (Steps S23 and S24). Operations of Steps S22 to S24 are similar to those of Steps S3 to S5 (see FIG. 6) in the first embodiment. Until the timing of end of the constant velocity movement comes, the image capture driving unit 23 does not stop the movement of the image capturing unit 22, and the image capturing unit 22 repeatedly carries out image capture while moving with constant velocity. When the image capture has been carried out in Step S24, the image capturing unit 22 outputs, to the defect determining unit 32, the captured image and the position of the image capturing unit 22 at the time of the image capture. Whether or not a given period of time has elapsed (Step S23) may be determined by the unit other than the image capturing unit 22 (e.g., the image capture driving unit 23), and the image capturing unit 22 may be allowed to carry out image capture upon lapse of the given period of time.

When the timing of end of the constant velocity movement has come (Yes in Step S22), the image capture driving unit 23 stops the constant velocity movement of the image capturing unit 2 (Step S25).

Subsequently, the image capture driving determining unit 23 determines whether or not there is any region for which image capture has not been carried out yet within the horizontal plane (Step S26). In other words, it is determined whether or not there is any region which has not entered the image capture range yet within the horizontal plane. This determination process is similar to that performed in Step S8 (see FIG. 6) in the first embodiment. When there is no region for which image capture has not been carried out (No in Step S26), the processing is brought to an end.

When there is a region for which image capture has not been carried out yet (Yes in Step S26), the image capture driving unit 23 horizontally moves the image capturing unit 22 (Step S27). In this step, the image capture driving unit 23 moves the image capturing unit 22 so that the image capture range before the horizontal movement and the image capture range after the horizontal movement partially overlap one another within the horizontal plane.

Thereafter, the processes of Steps S21 to S27 are repeated until it is determined in Step S26 that there is no region for which image capture has not been carried out within the horizontal plane. When the processing is returned to Step S21, the image capturing unit 22 is moved with constant velocity in the direction opposite to that of the previous movement in Step S21. For example, when the image capturing unit 22 has been previously moved downward in Step S21 and the image capturing unit 22 has been brought close to the upper surface of the transparent body 17, the image capturing unit 21 may be moved upward with constant velocity. On the other hand, when the image capturing unit 22 has been previously moved upward in Step S21, the image capturing unit 22 may be moved downward with constant velocity.

As a result of the above-described processing, a group of color images for the inside of the transparent body 17 is obtained for each image capture region located along the horizontal direction. This image group includes images captured while the depth inside the transparent body 17 is changed at regular intervals. Using the color images, the defect determining unit 32 determines existence or nonexistence of each of a scattering defect, a light-blocking defect and a polarization cancellation defect, and determines, when the defect exists, the depth of a position inside the transparent body 17 at which the defect exists.

Hereinafter, how the light of each wavelength travels will be described. When the blue light applied from the first light source 24 has reached a scattering defect, the blue light is scattered in each direction therefrom. Further, when no scattering defect exists, the blue light travels through the transparent body 17, and no light traveling toward the image capturing unit 22 is produced. Hence, when a scattering defect exists, blue pixels in a color image include a pixel having brightness higher than that of surrounding blue pixels.

When the P wave of green light applied from the second light source 25 has reached a light-blocking defect, the P wave of green light is blocked by this defect. On the other hand, when no light-blocking defect exists, the P wave of green light passes through the transparent body 17 and the polarized light beam splitter 28 and reaches the image capturing unit 22. Hence, when a light-blocking defect exists, green images in a color image include a pixel having brightness lower than that of surrounding green pixels.

When the P wave of red light applied from the second light source 25 has reached a polarization cancellation defect, the P wave of red light is subjected to optical rotation by this defect to produce an S wave. The S wave of red light passes through the polarized light beam splitter 28 and reaches the image capturing unit 22. On the other hand, when no polarization cancellation defect exists, the P wave of red light passes through the transparent body 17 without being subjected to optical rotation, and is reflected by the polarized light beam splitter 28; therefore, the P wave of red light will not reach the image capturing unit 22. Hence, when a polarization cancellation defect exists, red pixels in a color image include a pixel having brightness higher than that of surrounding red pixels.

The defect determining unit 32 makes comparisons on brightness of respective blue pixels of an image, and when the brightness is uniformly low (e.g., when the brightness is lower than a predetermined scattering determination threshold value), it is determined that no scattering defect exists within the depth of field at the time of capture of this image.

Further, the defect determining unit 32 makes comparisons on brightness of respective blue pixels of an image, and when the brightness of part of the pixels included in the blue pixels is higher than that of the surrounding blue pixels, it is determined that a scattering defect exists. For example, when the brightness of part of the blue pixels is equal to or higher than the scattering determination threshold value and the brightness of the surrounding blue pixels is lower than the scattering determination threshold value, it is determined that a scattering defect exists. Furthermore, the defect determining unit 32 determines that the scattering defect exists within the depth of field at the time of capture of this image. However, when such images are continuous, the defect determining unit 32 determines that a scattering defect exists within the depth of field at the time of capture of the image having the highest blue contrast among the continuous images (defective capture images), and that no scattering defect exists within the depth of field at the time of capture of the other defective capture images.

Moreover, the defect determining unit 32 makes comparisons on brightness of respective green pixels of an image, and when the brightness is uniformly high (e.g., when the brightness is higher than a predetermined light blockage determination threshold value), it is determined that no light-blocking defect exists within the depth of field at the time of capture of this image. Further, the defect determining unit 32 makes comparisons on brightness of respective green pixels of an image, and when the brightness of part of the pixels included in the green pixels is lower than that of the surrounding green pixels, it is determined that a light-blocking defect exists. For example, when the brightness of part of the green pixels is equal to or lower than the light blockage determination threshold value and the brightness of the surrounding green pixels is higher than the light blockage determination threshold value, it is determined that a light-blocking defect exists. Furthermore, the defect determining unit 32 determines that the light-blocking defect exists within the depth of field at the time of capture of this image. However, when such images are continuous, the defect determining unit 32 determines that a light-blocking defect exists within the depth of field at the time of capture of the image having the highest green contrast among the continuous images (defective capture images), and that no light-blocking defect exists within the depth of field at the time of capture of the other defective capture images.

The defect determining unit 32 makes comparisons on brightness of respective red pixels of an image, and when the brightness is uniformly low (e.g., when the brightness is lower than a predetermined polarization cancellation determination threshold value), it is determined that no polarization cancellation defect exists within the depth of field at the time of capture of this image. Further, the defect determining unit 32 makes comparisons on brightness of respective red pixels of an image, and when the brightness of part of the pixels included in the red pixels is higher than that of the surrounding red pixels, it is determined that a polarization cancellation defect exists. For example, when the brightness of part of the red pixels is equal to or higher than the polarization cancellation determination threshold value and the brightness of the surrounding red pixels is lower than the polarization cancellation determination threshold value, it is determined that a polarization cancellation defect exists. Furthermore, the defect determining unit 32 determines that the polarization cancellation defect exists within the depth of field at the time of capture of this image. However, when such images are continuous, the defect determining unit 32 determines that a polarization cancellation defect exists within the depth of field at the time of capture of the image having the highest red contrast among the continuous images (defective capture images), and that no polarization cancellation defect exists within the depth of field at the time of capture of the other defective capture images.

Also in the second embodiment, effects similar to those obtained by the first embodiment are obtained. Moreover, for each type of the defect, the corresponding light wavelength is decided in the second embodiment. In addition, the light of the three types of wavelengths is simultaneously applied to the transparent body 17, and existence or nonexistence of the three types of defects is determined based on brightness of pixels with colors corresponding to the respective wavelengths. Accordingly, it is possible to make a determination for each of the three types of defects from images of the transparent body 17 captured by the image capturing unit 22 while it is moved with constant velocity. Therefore, as compared with the first embodiment, the amount of movement of the image capturing unit 22 can be reduced and the time required to acquire all images used for inspection can be reduced.

Further, the determination result registration unit 51 and the result storage unit 52, which have been described in the variation (FIG. 16) of the first embodiment, may also be provided in the second embodiment.

Furthermore, as described in the other variation of the first embodiment, the defect determining unit 12 may detect a foreign substance existing at the upper surface of the transparent body 17 in such a manner that the foreign substance is distinguished from a defect. For example, when images having nonuniform brightness of pixels are continuous in a plurality of images obtained by carrying out image capture more than once while the image capturing unit 2 is moved in one direction and the contrast of the images is monotonously reduced or monotonously increased, the defect determining unit 12 may determine that a foreign substance exists at the upper surface of the transparent body 17.

Alternatively, a captured image of a defect existing inside the transparent body and a captured image of a foreign substance existing at the upper surface of the transparent body may be stored in the transparent body inspecting device. Moreover, when an image having nonuniform brightness is obtained, the defect determining unit 12 may compare the obtained image with a defect image and a foreign substance image, which are prepared in advance, to determine which of the probability of correspondence of the obtained image to the defect image and the probability of correspondence of the obtained image to the foreign substance image is higher, and may thus detect a foreign substance based on this determination.

Alternatively, in each of the foregoing embodiments, instead of performing inspection for the three types of defects, the transparent body inspecting device may perform inspection for two types of defects such as a scattering defect and a light-blocking defect, or may perform inspection for two types of defects such as a scattering defect and a polarization cancellation defect. For example, in the second embodiment, the transparent body inspecting device may perform inspection for a scattering defect and a light-blocking defect without applying a P wave of the third wavelength. Alternatively, in the second embodiment, the transparent body inspecting device may perform inspection for a scattering defect and a polarization cancellation defect without applying a P wave of the second wavelength.

Note that the following features of the transparent body inspecting device are provided in each of the foregoing embodiments.

A transparent body inspecting device includes: a light application unit (e.g., the first light source 4 or the second light source 5) for applying light to a transparent body; an image capturing unit (e.g., the image capturing unit 2) which captures an image of the transparent body and in which a depth of field is smaller than a height of the transparent body; an image capture driving unit (e.g., the image capture driving unit 3) for moving the image capturing unit in a direction in which the image capturing unit is brought close to the transparent body and in a direction in which the image capturing unit is brought away from the transparent body; and a defect determining unit (e.g., the defect determining unit 12) for determining existence or nonexistence of a defect in the transparent body based on whether or not brightness of pixels in the image captured by the image capturing unit is nonuniform, wherein the image capturing unit carries out image capture more than once while moving in the direction in which the image capturing unit is brought close to the transparent body or in the direction in which the image capturing unit is brought away from the transparent body, and wherein when the brightness of pixels in the image captured by the image capturing unit is nonuniform, the defect determining unit determines that a defect exists within the depth of field at the time of capture of this image.

Furthermore, a transparent body inspecting device includes: an image capturing unit (e.g., the image capturing unit 2) for capturing an image of a transparent body; a first light application unit (e.g., the first light source 4) for applying light to the transparent body from a lateral position; a second light application unit (e.g., the second light source 5) for applying light to the transparent body from a position located opposite to the image capturing unit, with the transparent body sandwiched between the image capturing unit and the second light application unit; and a defect determining unit (e.g., the defect determining unit 12) for determining existence or nonexistence of a defect in the transparent body based on whether or not brightness of pixels in the image captured by the image capturing unit is nonuniform, wherein the defect determining unit determines whether or not the brightness of pixels in the image, captured in a state in which light is applied to the transparent body by the first light application unit, is nonuniform, and also determines whether or not the brightness of pixels in the image, captured in a state in which light is applied to the transparent body by the second light application unit, is nonuniform, thus determining existence or nonexistence of a plurality of types of defects.

The present invention has been described in detail with reference to the particular embodiments, but it is apparent to those skilled in the art that various changes and modifications may be made without departing from the sprit and scope of the present invention.

The present application is based on Patent Application No. 2008-297112 filed in Japan on Nov. 20, 2008, and Patent Application No. 2008-297113 filed in Japan on Nov. 20, 2008, the contents of which are hereby incorporated by reference.

INDUSTRIAL APPLICABILITY

The present invention is suitably applied to a transparent body inspecting device for performing inspection for a defect in a transparent body having no birefringence.

DESCRIPTION OF REFERENCE NUMERALS AND SIGNS 1 support unit
2 image capturing unit 3 image capture driving unit
4 first light source
5 second light source
6 application unit
7 light source side polarizing plate
8 image capture side polarizing plate
10 polarizing plate driving unit
11 switching unit
12 defect determining unit
13 point light source

The invention claimed is:

1. A transparent body inspecting device comprising:
at least one light source to apply light to a transparent body;
a camera to capture an image of the transparent body, the camera having a depth of field being smaller than a height of the transparent body;
a driving device physically coupled to the camera to move the camera in a direction in which the camera is brought close to the transparent body and in a direction in which the camera is brought away from the transparent body; and
a defect determining unit communicatively coupled to the camera such that the defect determining unit receives image data of the captured image from said camera to determine existence or nonexistence of a defect in the transparent body based on whether or not brightness of pixels in the image captured by the camera is nonuniform, wherein:
the camera carries out image capture more than once while moving in the direction in which the camera is brought close to the transparent body or in the direction in which the camera is brought away from the transparent body;
when the brightness of pixels in the image captured by the camera is nonuniform, the defect determining unit determines that a defect exists within the depth of field at the time of capture of this image; and
when defective capture images having nonuniform brightness of pixels are continuous in a plurality of the images captured by the camera while the camera is moved in one direction, the defect determining unit determines that a defect exists within the depth of field at the time of capture of the defective capture image having the highest contrast among the defective capture images.

2. The transparent body inspecting device according to claim 1, wherein:
when the camera is moved in the direction in which the camera is brought close to the transparent body and in the direction in which the camera is brought away from the transparent body, the camera moves the image capturing unit with constant velocity; and
the camera captures images of the transparent body while moving with constant velocity.

3. The transparent body inspecting device according to claim 1, wherein:
the at least one light source comprises a lateral wall which is perpendicular to an upper surface of the transparent body and on which a plurality of point light sources are arranged; and
a point light source at an end portion close to the camera is located closer to the camera than a surface of the transparent body, which faces toward the camera, and a point light source at an end portion away from the camera is located further away from the camera than a surface of the transparent body, which is opposite to the camera.

4. The transparent body inspecting device according to claim 3, wherein:
the plurality of point light sources are aligned in a plurality of rows and arranged so that positions of the point light sources in the adjacent rows are deviated from each other.

5. A transparent body inspection method
comprising: applying light to a transparent body;
capturing a plurality of images of the transparent body while a camera in which a depth of field is smaller than a height of the transparent body is moved in a direction in which the camera is brought close to the transparent body and in a direction in which the camera is brought away from the transparent body;
determining, when brightness of pixels in the image captured by the camera is nonuniform, that a defect exists within the depth of field at the time of capture of this image; and
determining, when defective capture images having nonuniform brightness of pixels are continuous in a plurality of the images captured by the camera while the camera is moved in one direction, that a defect exists within the depth of field at the time of capture of the defective capture image having the highest contrast among the defective capture images.

* * * * *